United States Patent
Qi et al.

(10) Patent No.: US 12,048,711 B2
(45) Date of Patent: *Jul. 30, 2024

(54) COMPOSITION AND USE THEREOF IN THE MANUFACTURE OF MEDICAMENT FOR TREATING CANCER

(71) Applicant: NEWISH TECHNOLOGY (BEIJING) CO., LTD., Beijing (CN)

(72) Inventors: Hailong Qi, Beijing (CN); Xiaofang Wang, Beijing (CN); Zhongjie Sun, Beijing (CN)

(73) Assignee: NEWISH TECHNOLOGY (BEIJING) CO., LTD., Beijing (CN)

( * ) Notice: Subject to any disclaimer, the term of this patent is extended or adjusted under 35 U.S.C. 154(b) by 614 days.

This patent is subject to a terminal disclaimer.

(21) Appl. No.: 17/309,485

(22) PCT Filed: Aug. 19, 2020

(86) PCT No.: PCT/CN2020/109969
§ 371 (c)(1),
(2) Date: Jun. 1, 2021

(87) PCT Pub. No.: WO2022/007136
PCT Pub. Date: Jan. 13, 2022

(65) Prior Publication Data
US 2022/0323470 A1    Oct. 13, 2022

(30) Foreign Application Priority Data

Jul. 6, 2020  (CN) .......................... 202010643576.5

(51) Int. Cl.
| | | |
|---|---|---|
| *A61P 35/00* | (2006.01) | |
| *A61K 9/00* | (2006.01) | |
| *A61K 31/7034* | (2006.01) | |
| *A61K 45/06* | (2006.01) | |

(52) U.S. Cl.
CPC ........ *A61K 31/7034* (2013.01); *A61K 9/0053* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 2014/0235558 A1 | 8/2014 | Kim et al. |
| 2014/0336129 A1 | 11/2014 | Weihua |
| 2015/0111240 A1 | 4/2015 | Wamhoff et al. |
| 2020/0061028 A1 | 2/2020 | Hum et al. |
| 2021/0236501 A1 | 8/2021 | Cantley et al. |
| 2022/0305072 A1 | 9/2022 | Sun et al. |

FOREIGN PATENT DOCUMENTS

| | | | |
|---|---|---|---|
| CN | 101343296 | 1/2009 | |
| CN | 105358173 | 2/2016 | |
| CN | 110430876 A | 11/2019 | |
| JP | 2016520066 A | 7/2016 | |
| JP | 2016535591 A | 11/2016 | |
| JP | 2022542723 A | 10/2022 | |
| WO | WO-2014081660 A1 * | 5/2014 | ............... A61P 1/00 |
| WO | WO 2019232403 A1 | 12/2019 | |

OTHER PUBLICATIONS

Medlineplus, "Gefitinib", 2015, National Library of Medicine (Year: 2015).*
Cefalo et al., "Sotagliflozin, the first dual SGLT inhibitor: current outlook and perspectives", 2019, Cardiovascular Diabetology, 18, pp. 1-14 (Year: 2019).*
Ren et al., "EGFR-SGLT1 interaction does not respond to EGFR modulators, but inhibition of SGLT1 sensitizes prostate cancer cells to EGFR tyrosine kinase inhibitors," 2013, Prostate, 73(13), 1453-61 (Year: 2013).*
Office Communication issued in correspondence Japanese Application No. 2021-526666 dated Oct. 24, 2022 {English tanslation }.
Chen et al., "PKCδ-mediated SGLT1 upregulation confers the acquired resistance of NSCLC to EGFR TKIs." *Oncogene*, 40(29):4796-4808, 2021.
European Search Report issued in European Application No. 20886183. 1, dated Feb. 7, 2022.
Office Action issued in Chinese Application No. 202010643576.5, dated Apr. 26, 2022, and English language translation thereof.
Camidge et al., "Acquired resistance to TKIs in solid tumours: learning from lung cancer," *Nat. Rev. Clin. Oncol.*, advance online publication, Jul. 1, 2014. 9 pages. doi:10.1038/nrclinonc.2014.104.
Dominguez Rieg and Rieg, "What does sodium-glucose cotransporter 1 inhibition add: Prospects for dual inhibition," *Diabetes Obes. Metab.*, 21(Suppl. 2):43-52, 2019.
Flynn and Gerriets, "Imatinib," In: StatPearls [Internet], 25 pages, 2020. Available from: https://www.ncbi.nlm.nih.gov/books/NBK551676/.
Kroemer and Pouyssegur, "Tumor Cell Metabolism: Cancer's Achilles' Heel," *Cancer Cell*, 13:472-482, 2008.
Lemmon and Schlessinger, "Cell signaling by receptor tyrosine kinases," *Cell*, 141:1117-1134, 2010.
Minuti et al., "Protein kinase inhibitors to treat non-small-cell lung cancer," *Expert Opin. Pharmacother.*, 15(9):1203-1213, 2014.
Navale and Paranjape, "Glucose transporters: physiological and pathological roles," *Biophys. Rev.*, 8:5-9, 2016.
Thomas and Weihua, "Rethink of EGFR in cancer with its kinase independent function on board," *Frontiers in Oncology*, 9, Article 800, 25 pages, 2019.
Warburg, "On the Origin of Cancer Cells," *Science*, 123(3191):309-314, 1956.
Yarden and Pines, "The ERBB network: at last, cancer therapy meets systems biology," *Nat. Rev. Cancer*, 12(8):553-63, 2012.

(Continued)

*Primary Examiner* — Jeffrey H Murray
*Assistant Examiner* — Madeline E Braun
(74) *Attorney, Agent, or Firm* — Parker Highlander PLLC

(57) ABSTRACT

A composition containing a compound of formula I or a pharmaceutically acceptable salt, dimer or trimer thereof, and a tyrosine kinase activity inhibitor is provided. A method of preventing and/or treating cancer by administering a subject in need thereof the composition is provided. The combination of Sotagliflozin and a tyrosine kinase activity inhibitor may exhibit a synergistic inhibitory effect on tumors, and the efficacy of the combination is significantly better than that of a single drug.

8 Claims, 26 Drawing Sheets

(56) References Cited

OTHER PUBLICATIONS

Blessing and Weihua, "Abstract 989: Profiling the expression of SGLT in prostate cancer," *Cancer Res.*, 71(Supl. 8):989, 2011.

Huber et al., "EGFR-mediated stimulation of sodium/glucose cotransport promotes survival of irradiated human A549 lung adenocarcinoma cells," *Radiotherapy and Oncology*, 103:373-379, 2012.

Ren et al., "Synthetic lethality targeting LKB1 mutant and EGFR wild type human non-small cell lung cancer cells by glucose starvation and SLGT2 inhibition," bioR$_x$iv, doi: https://doi.org/10.1101/622126, 2019.

Tu, Chih-Yen, "The mechanisms between cigarette smoking and desensitizes epidermal growth factor receptor—expressing non-small cell lung cancer to epidermal growth factor receptor—tyrosine kinase inhibitors," National Chung Hsing University, Ph.D. dissertation, 2018.

English Translation of Office Action in Japanese Patent Application No. 2021-526666, mailed May 2, 2023.

Office Communication issued in correspondent European Application No. 20 886 183.1, dated Jul. 14, 2023.

Ren et al., EGFR-SGLT1 interaction does not respond to EGFR modulators, but inhibition of SGLT1 sensitizes prostate cancer cells to EGFR tyrosine kinase inhibitors, *Prostate*, 73(13):1453-61. doi: 10.1002/pros.22692, 2013.

\* cited by examiner

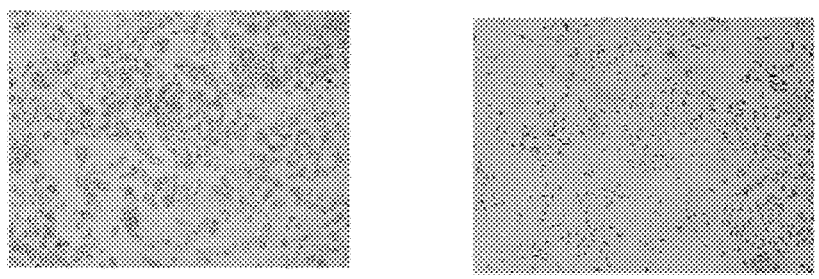
Fig 1
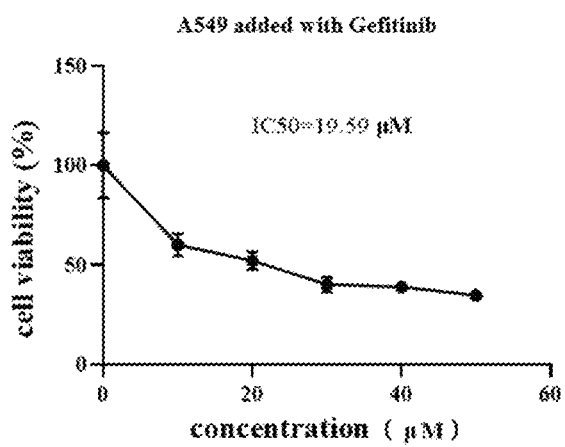
Fig 2-a-1
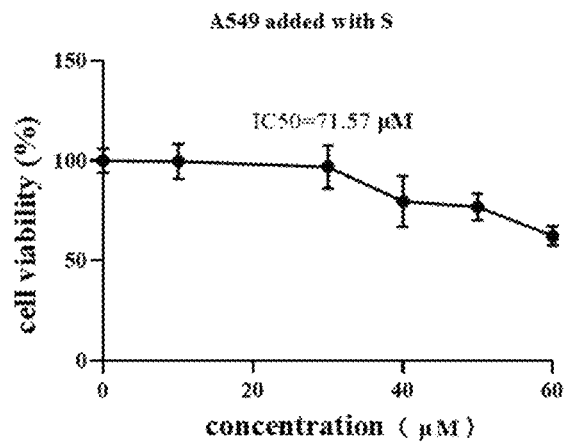
Fig 2-a-2
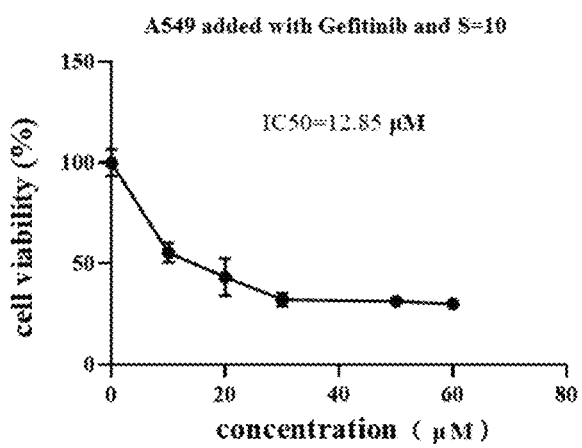
Fig 2-a-3
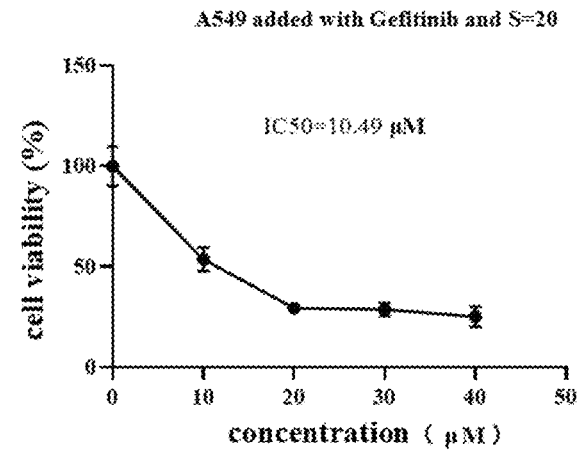
Fig 2-a-4

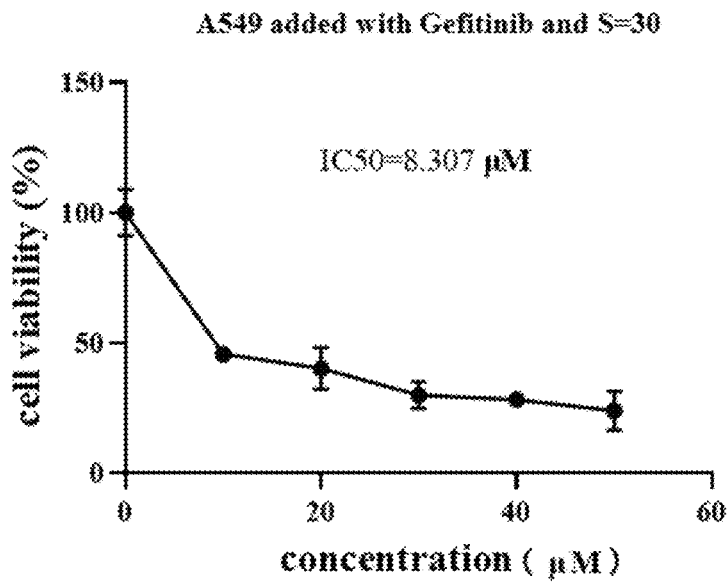
Fig 2-a-5
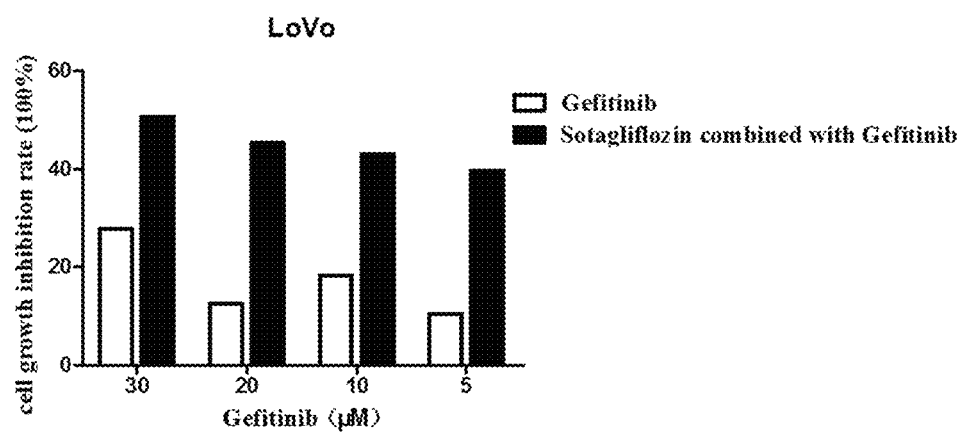
Fig 2-b
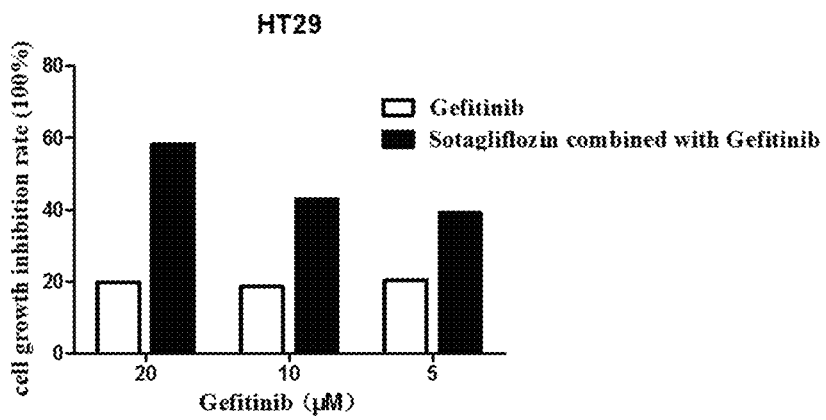
Fig 2-c

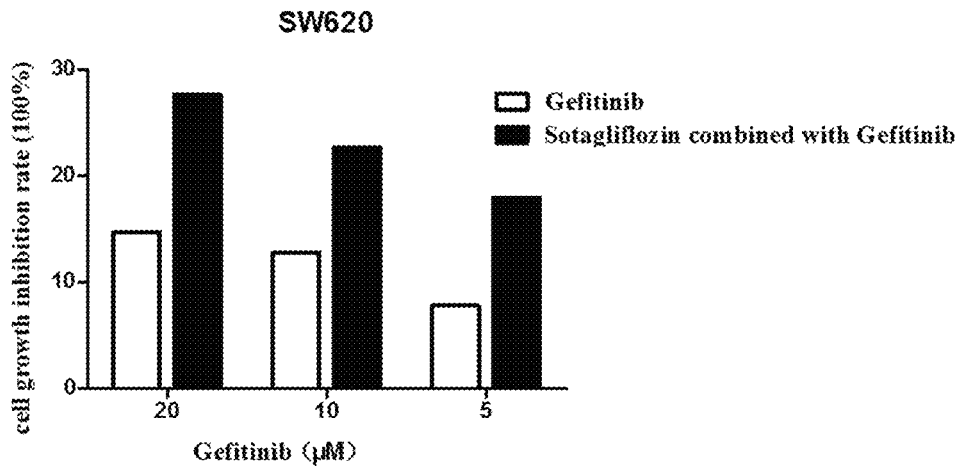
Fig 2-d
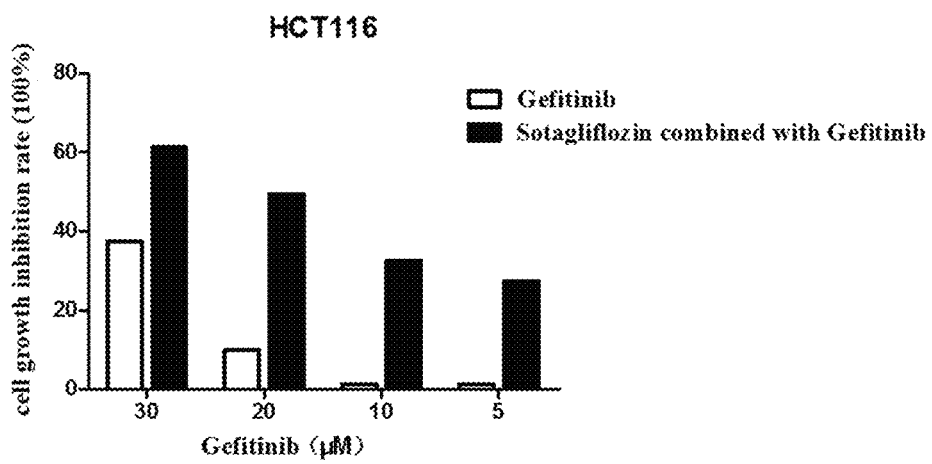
Fig 2-e
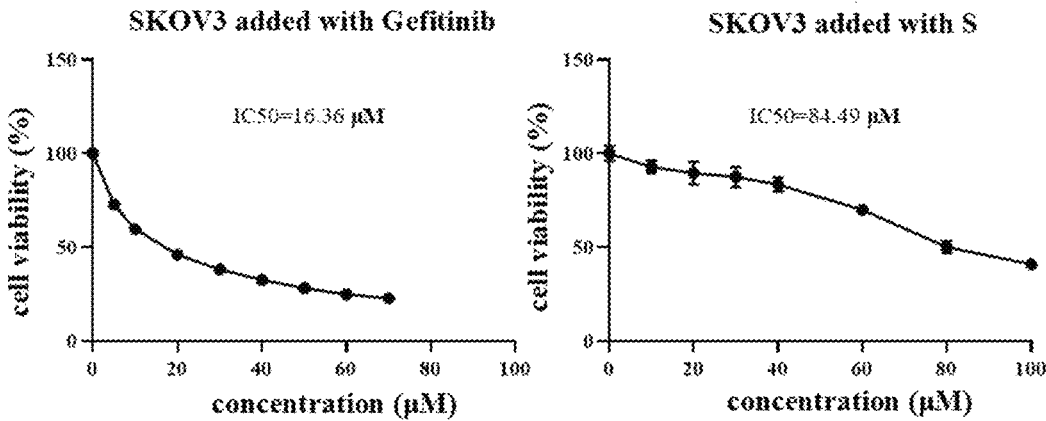
Fig 2-f-1    Fig 2-f-2

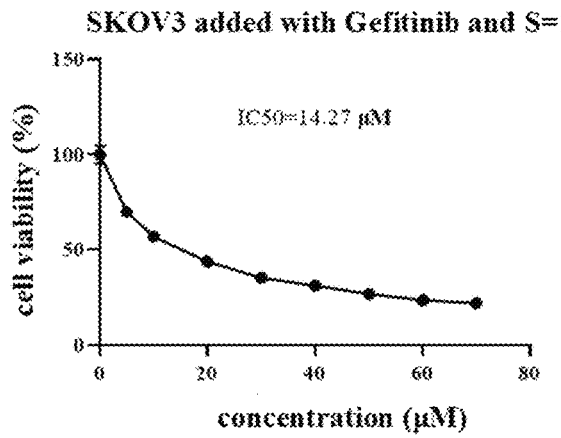
Fig 2-f-3
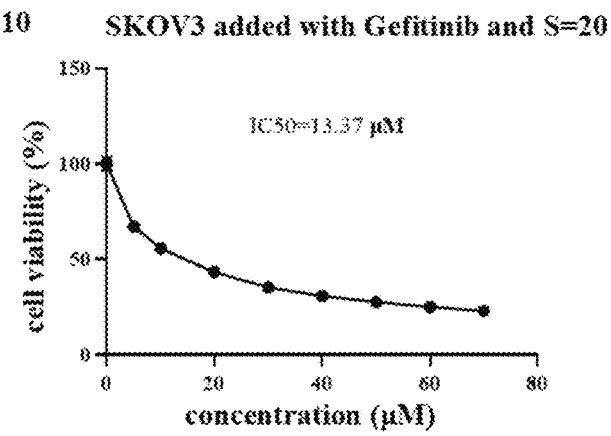
Fig 2-f-4
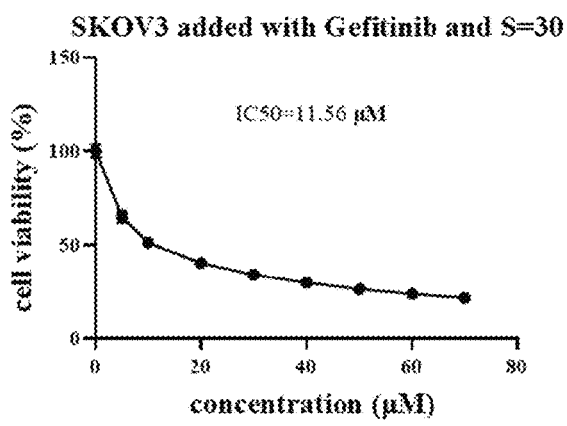
Fig 2-f-5
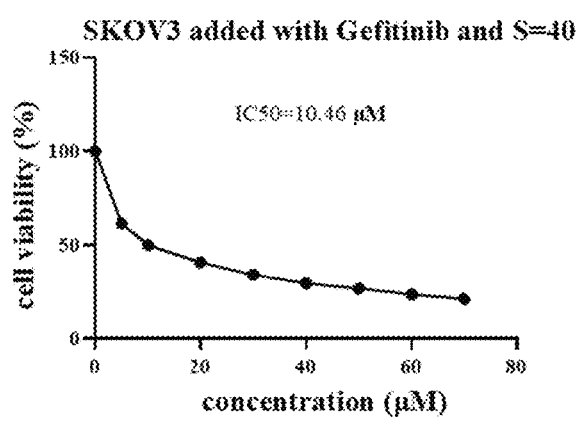
Fig 2-f-6
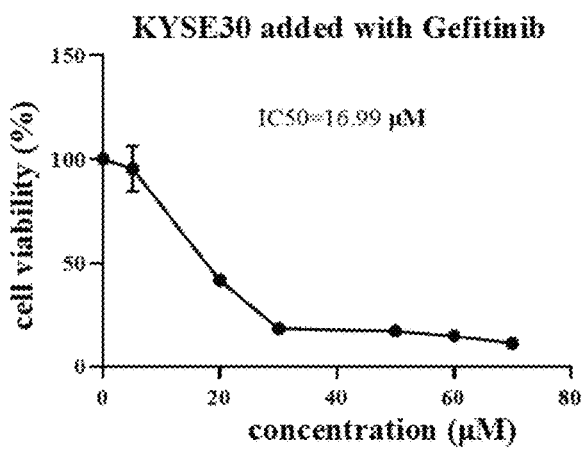
Fig 2-g-1
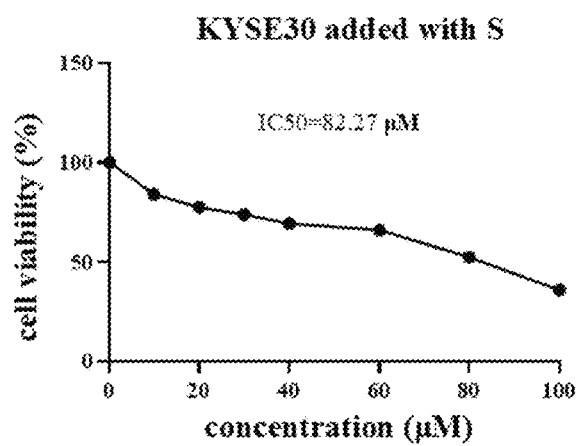
Fig 2-g-2

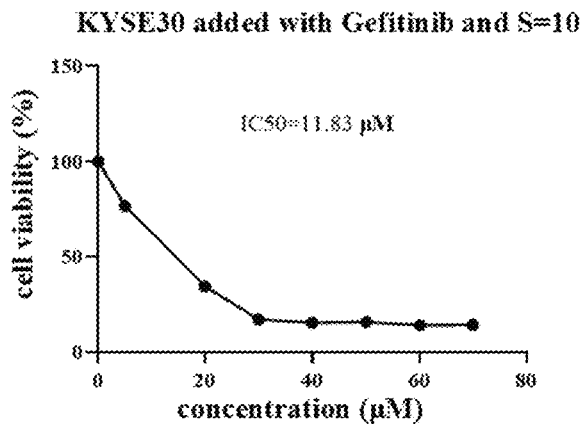
Fig 2-g-3
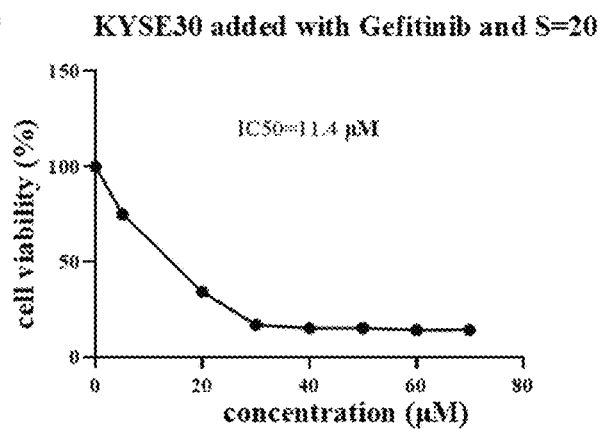
Fig 2-g-4
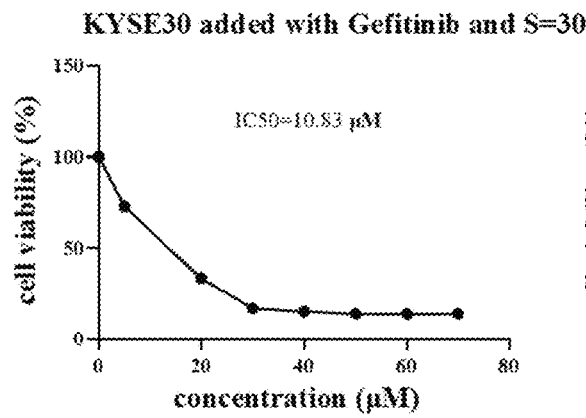
Fig 2-g-5
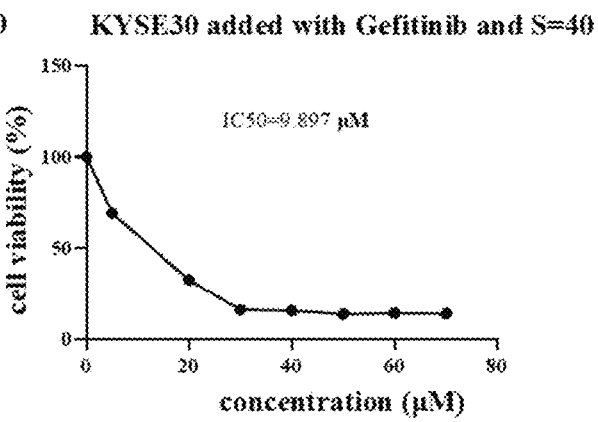
Fig 2-g-6
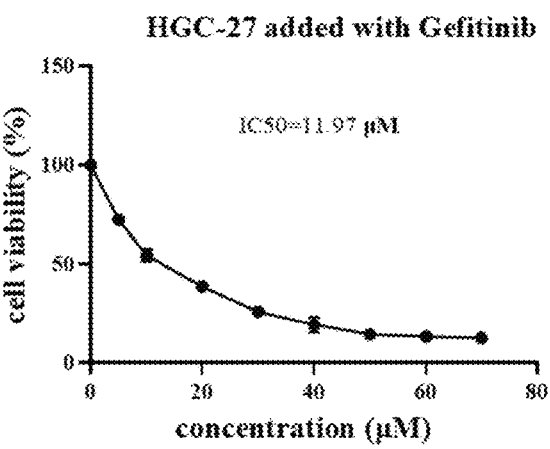
Fig 2-h-1
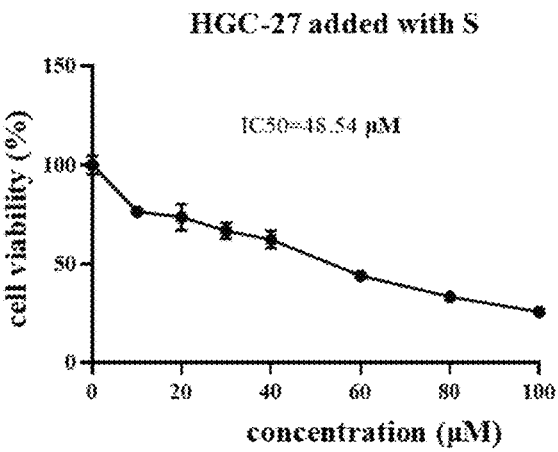
Fig 2-h-2

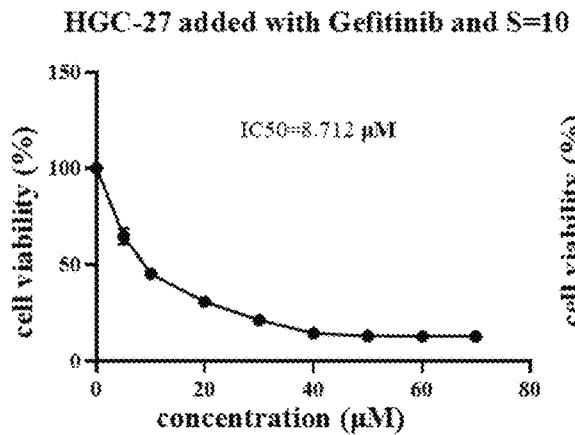
Fig 2-h-3
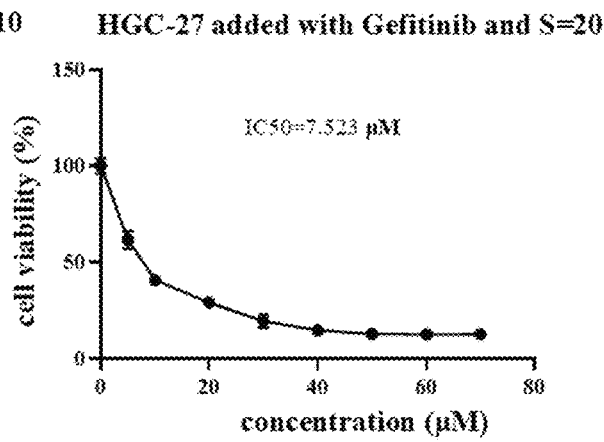
Fig 2-h-4
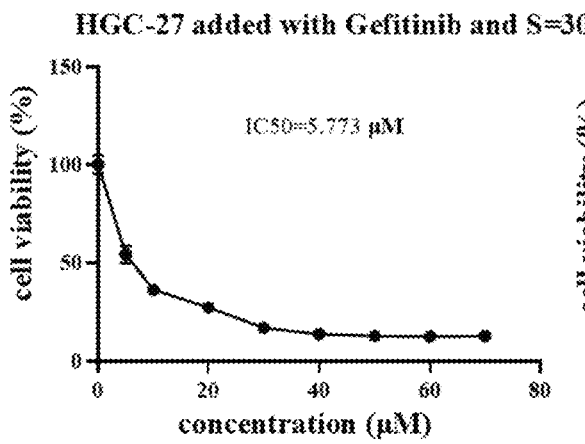
Fig 2-h-5
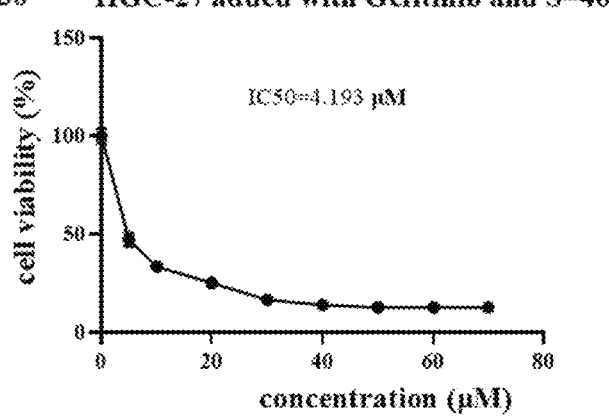
Fig 2-h-6
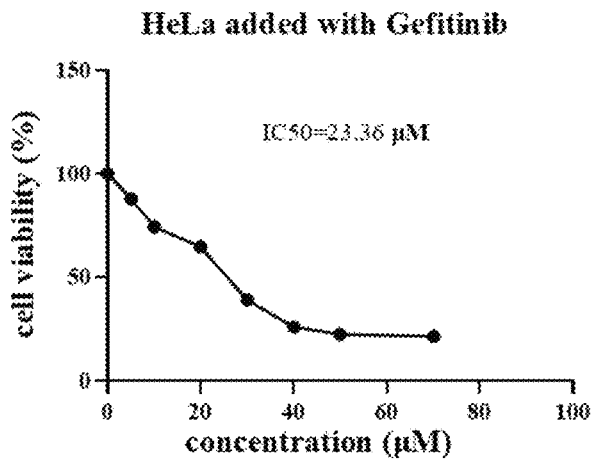
Fig 2-i-1
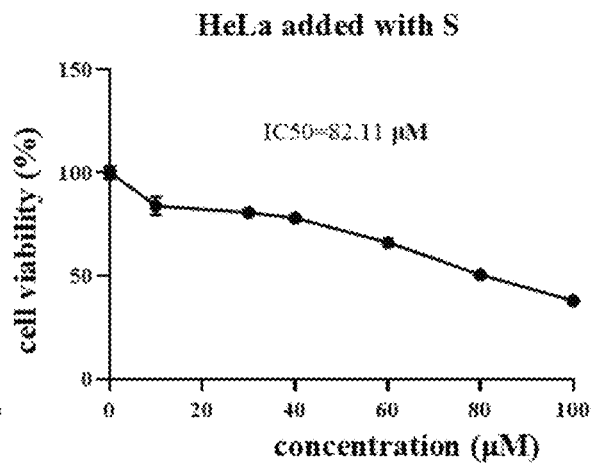
Fig 2-i-2

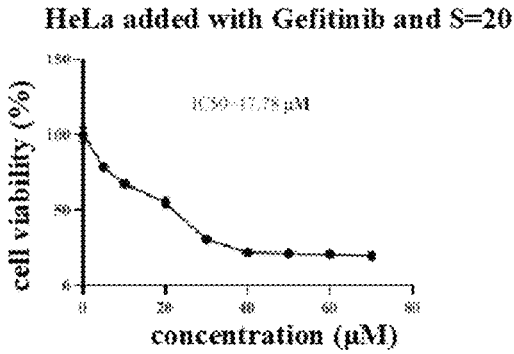
Fig 2-i-3
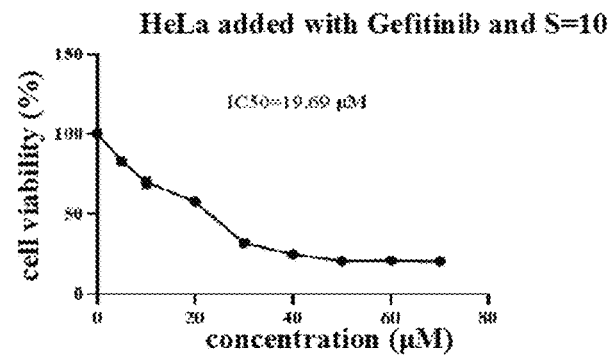
Fig 2-i-4
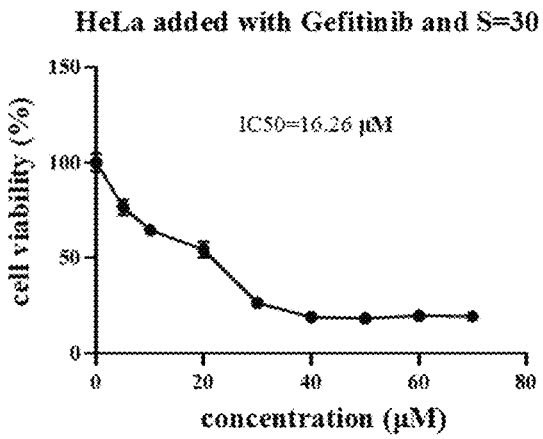
Fig 2-i-5
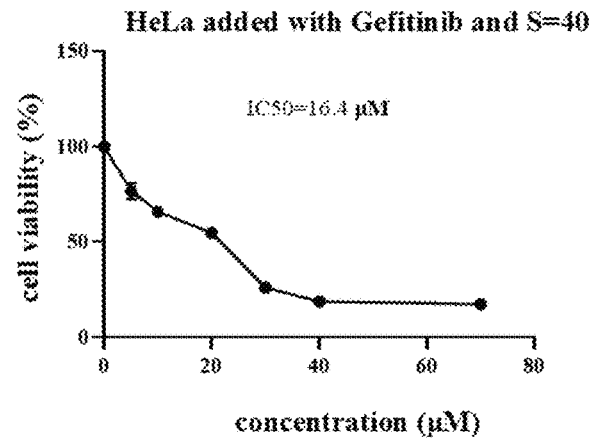
Fig 2-i-6
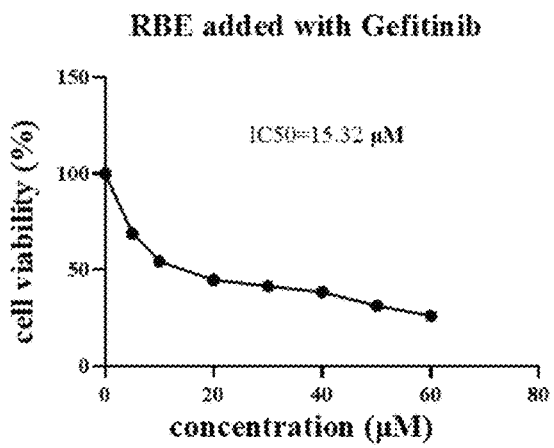
Fig 2-j-1
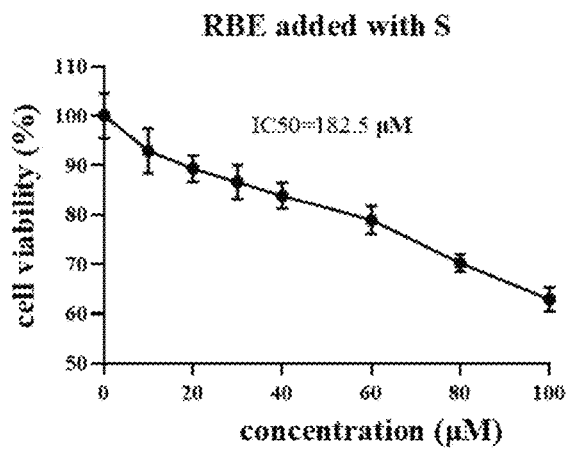
Fig 2-j-2

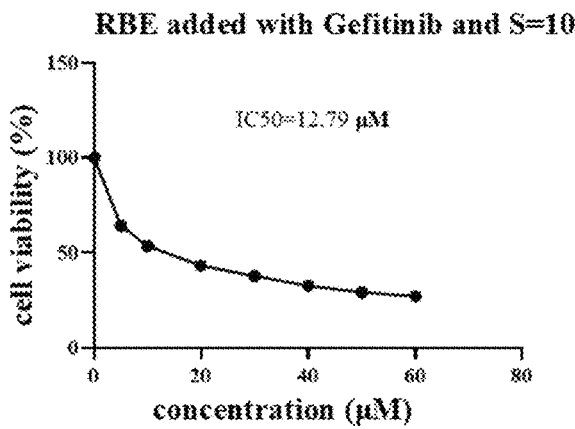
Fig 2-j-3
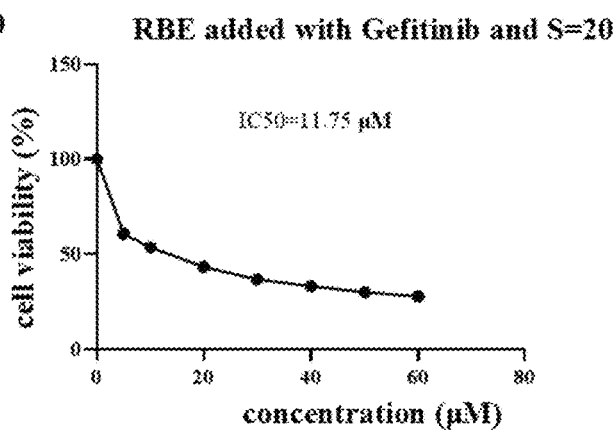
Fig 2-j-4
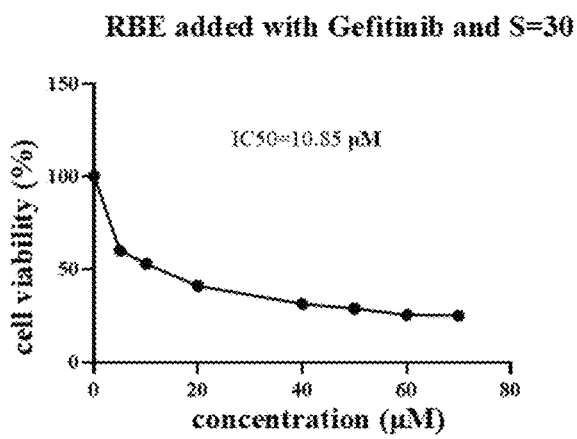
Fig 2-j-5
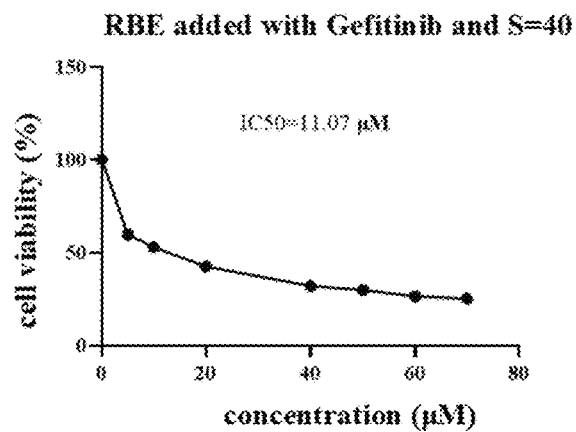
Fig 2-j-6
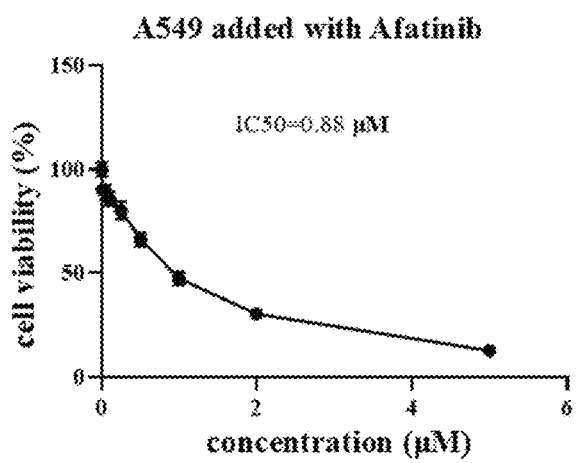
Fig 2-k-1
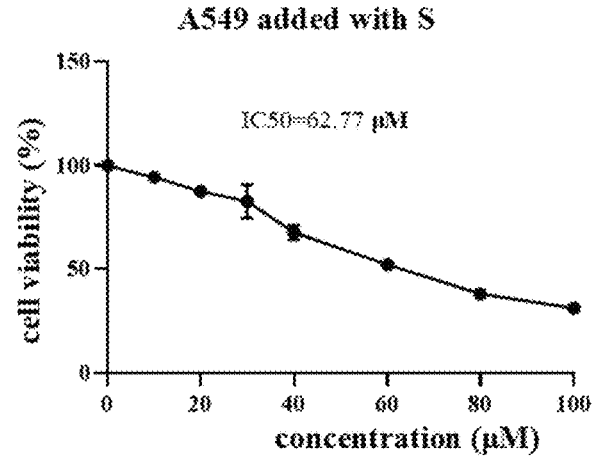
Fig 2-k-2

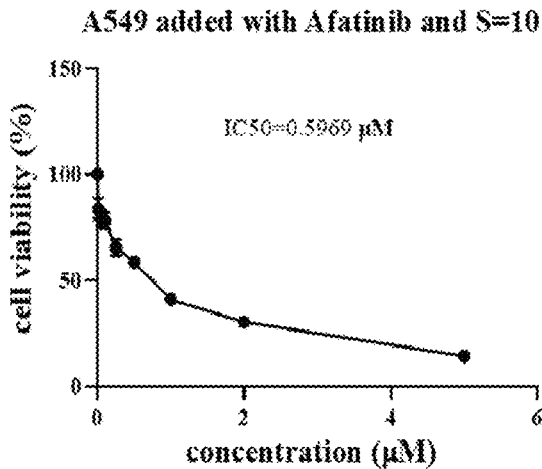
Fig 2-k-3
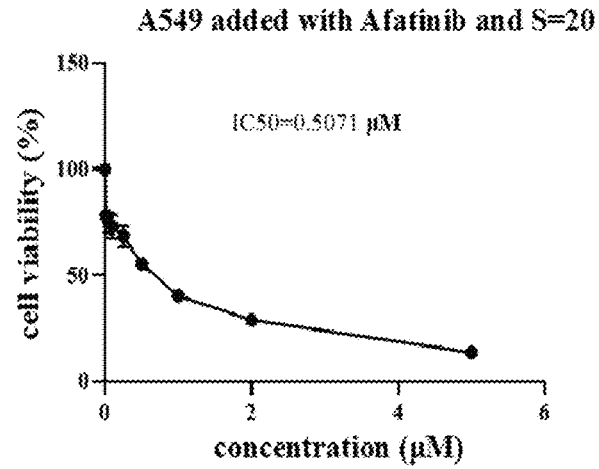
Fig 2-k-4
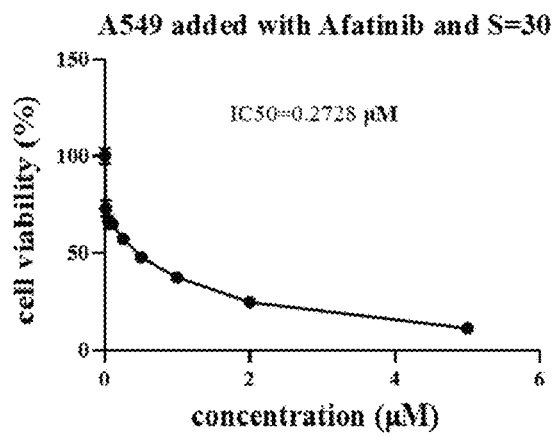
Fig 2-k-5
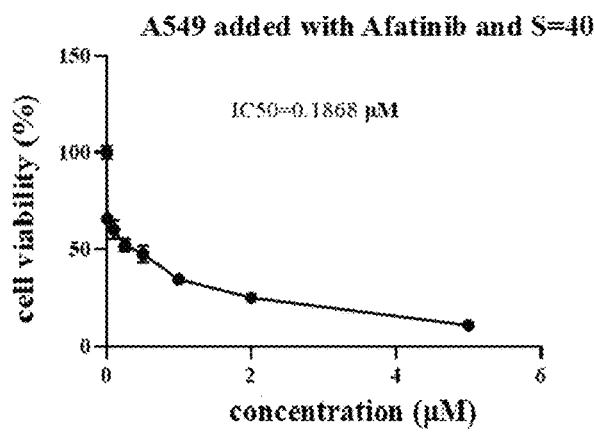
Fig 2-k-6
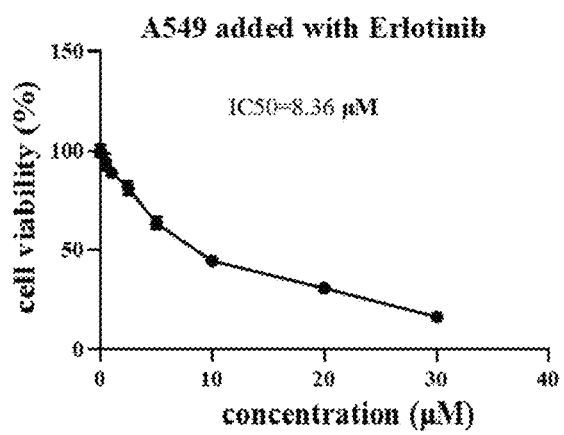
Fig 2-l-1
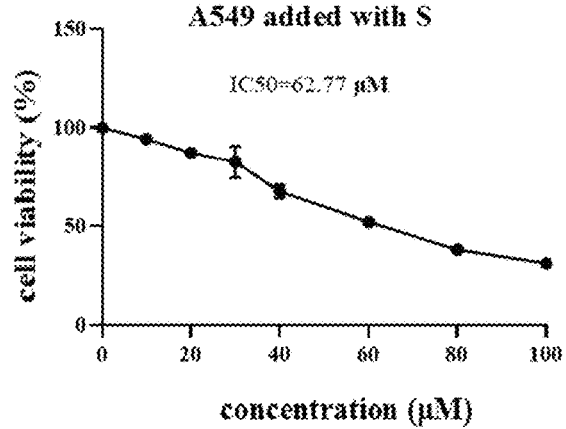
Fig 2-l-2

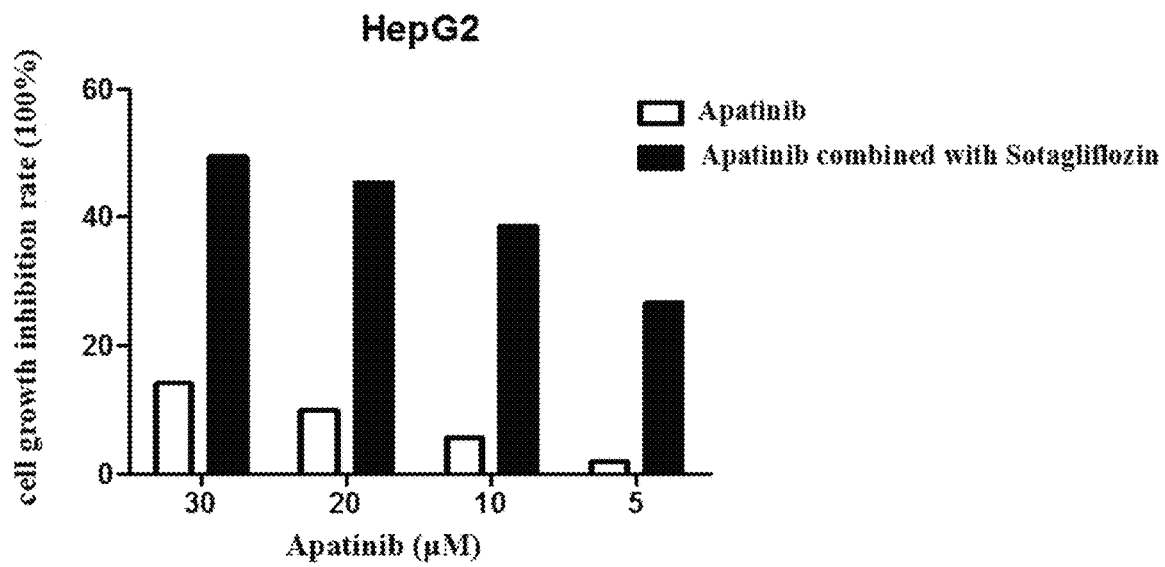
Fig 4-a-1
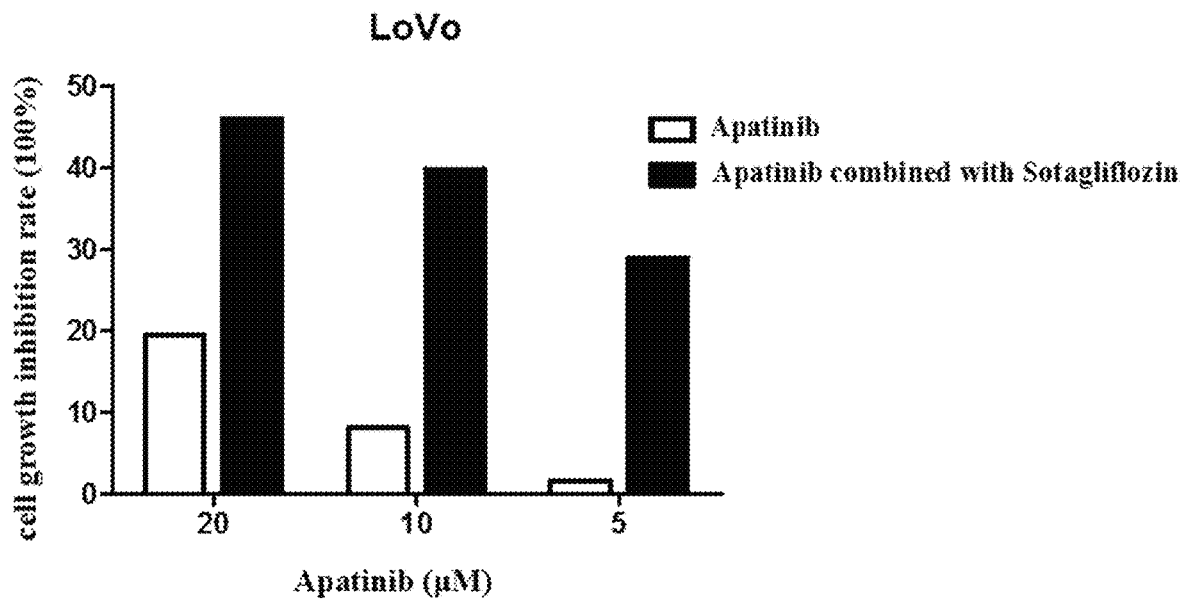
Fig 4-a-2

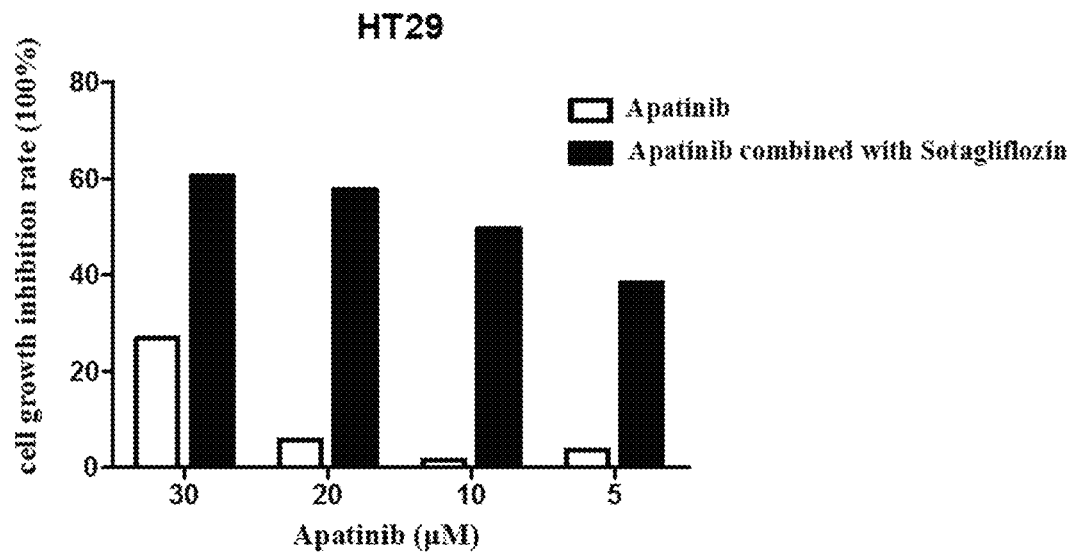
Fig 4-a-3
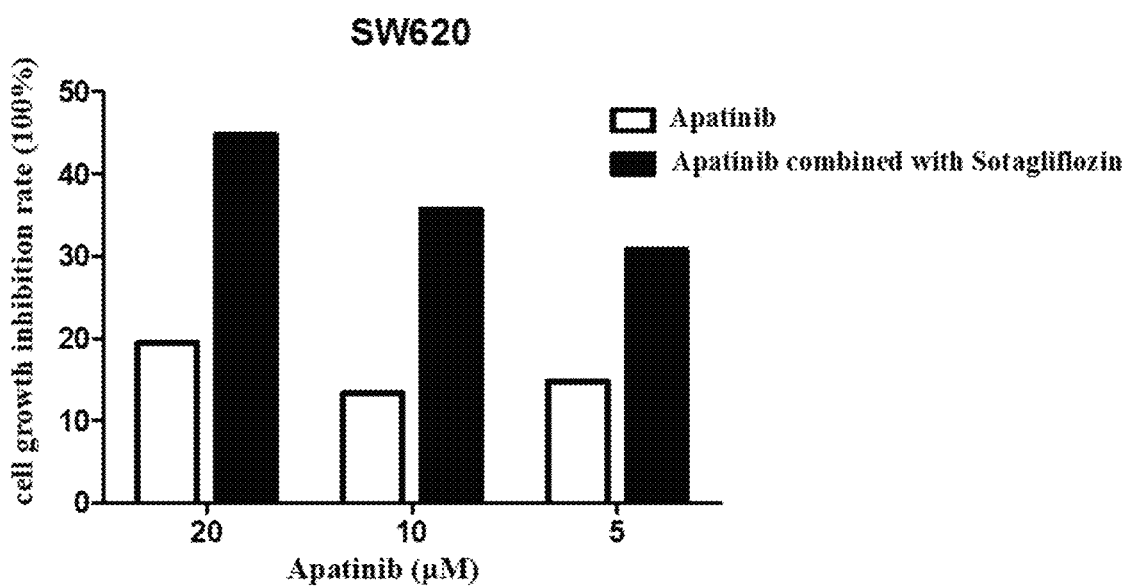
Fig 4-a-4

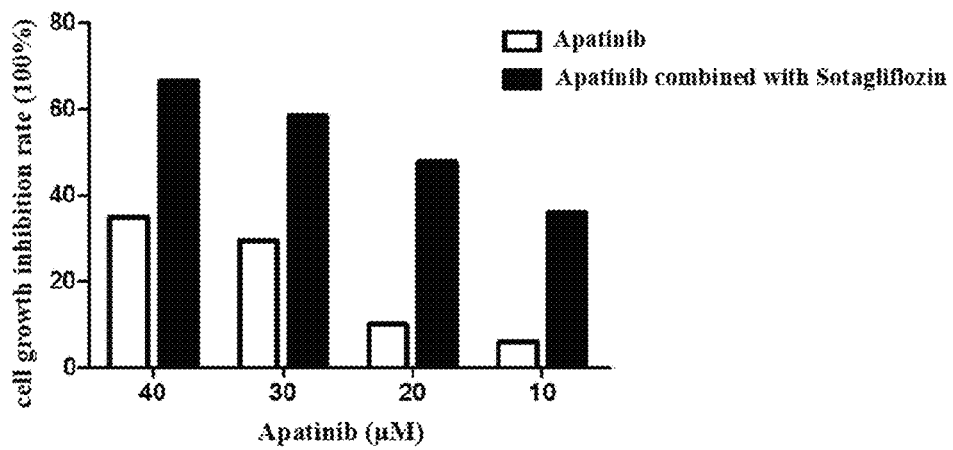
Fig 4-a-5
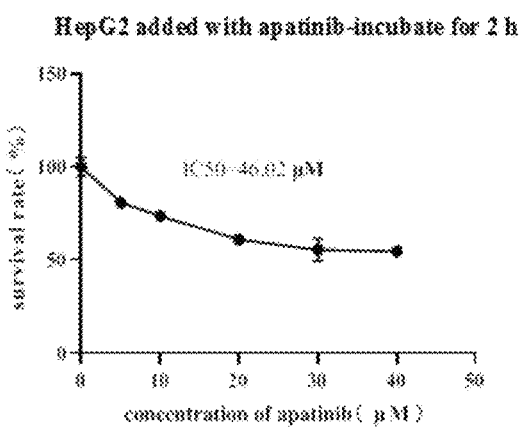
Fig 4-b-1
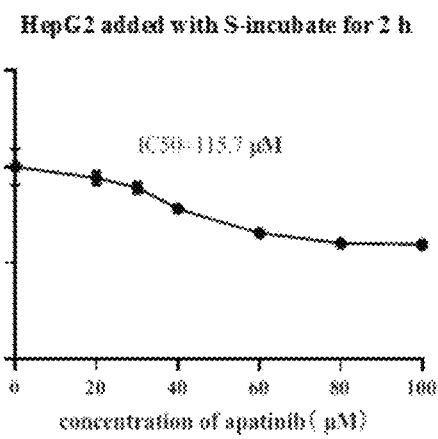
Fig 4-b-2
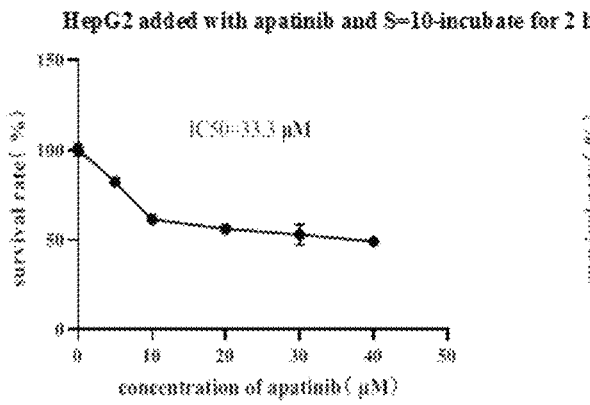
Fig 4-b-3
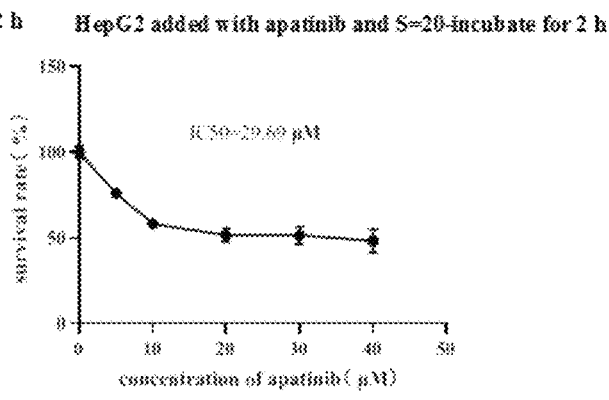
Fig 4-b-4

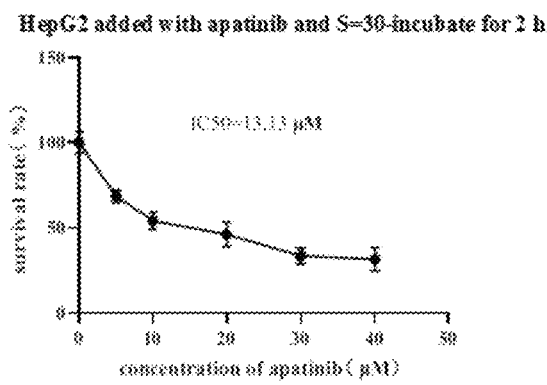
Fig 4-b-5
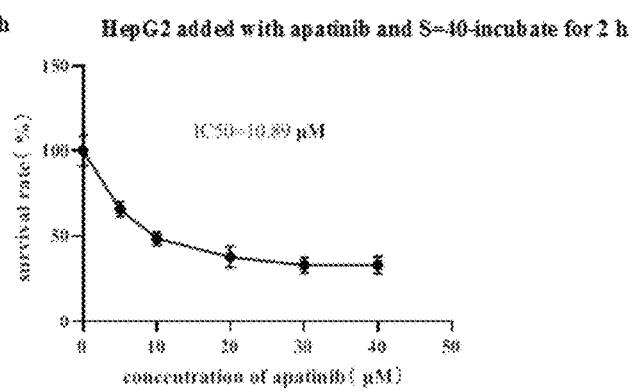
Fig 4-b-6
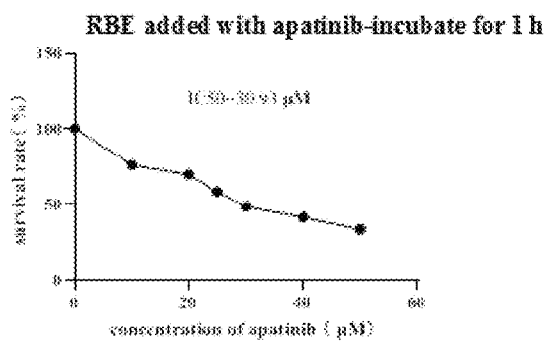
Fig 4-c-1
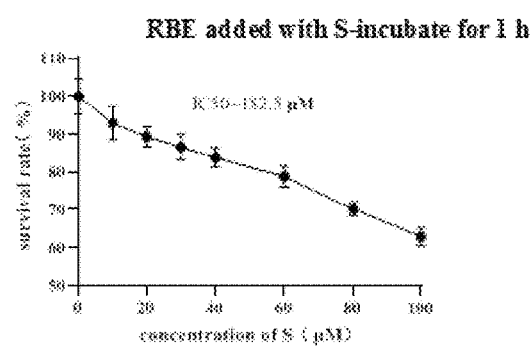
Fig 4-c-2
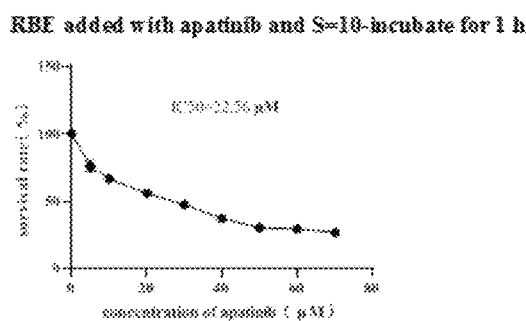
Fig 4-c-3
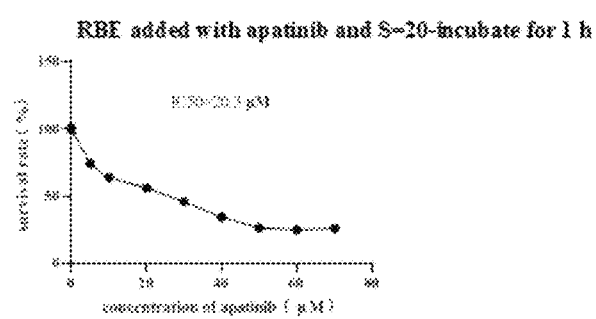
Fig 4-c-4

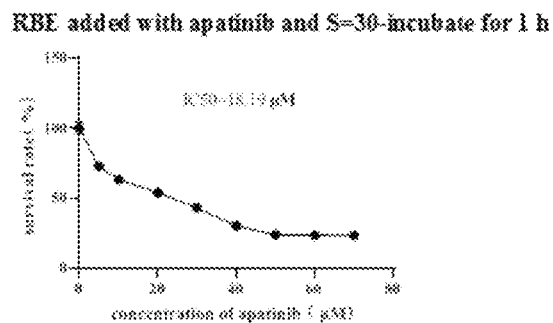
Fig 4-c-5
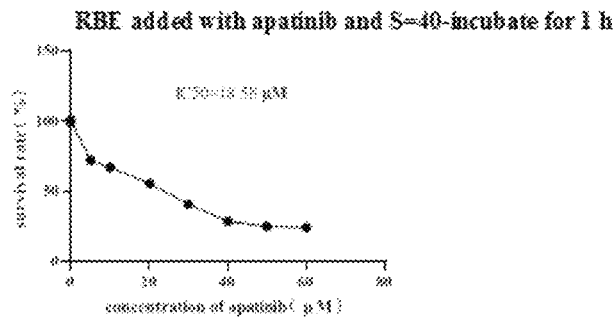
Fig 4-c-6
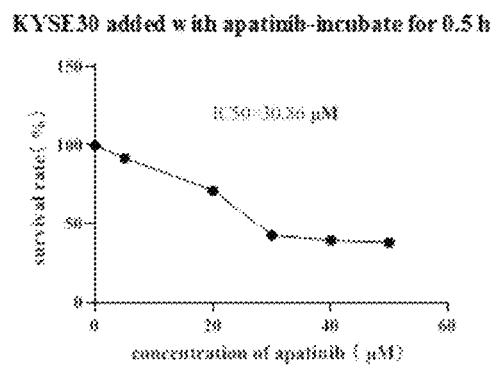
Fig 4-d-1
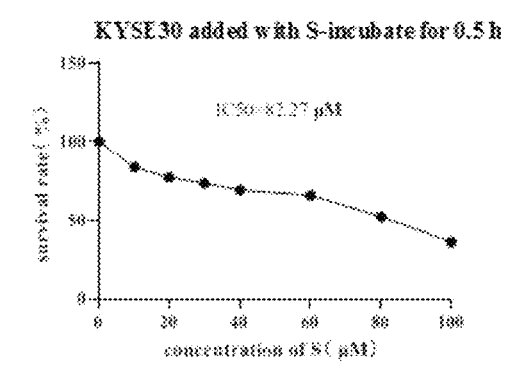
Fig 4-d-2
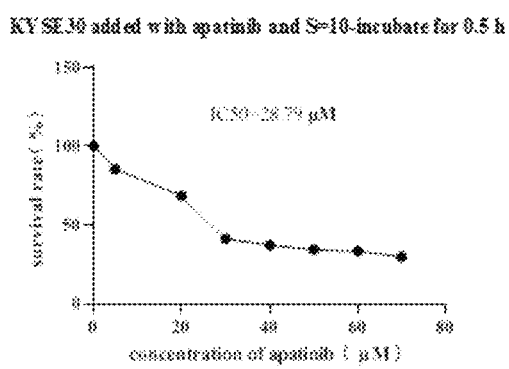
Fig 4-d-3
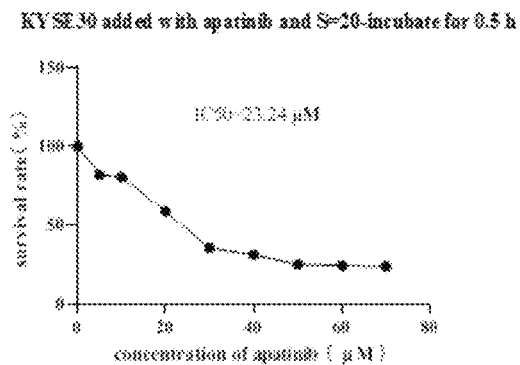
Fig 4-d-4

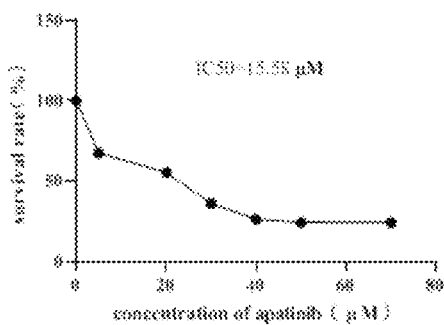
Fig 4-d-5
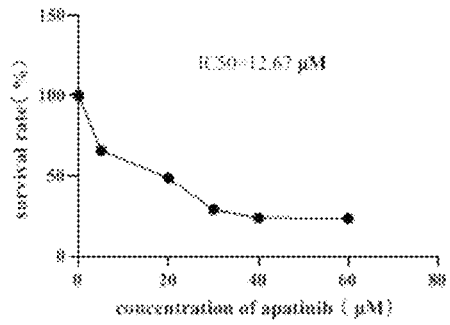
Fig 4-d-6
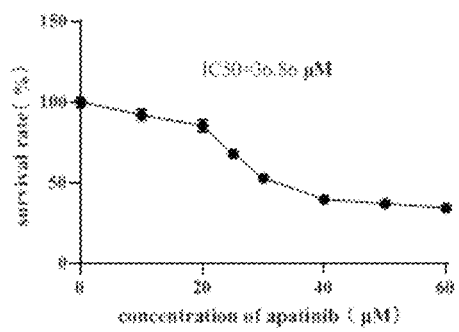
Fig 4-e-1
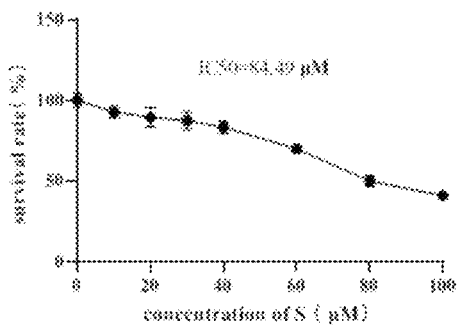
Fig 4-e-2
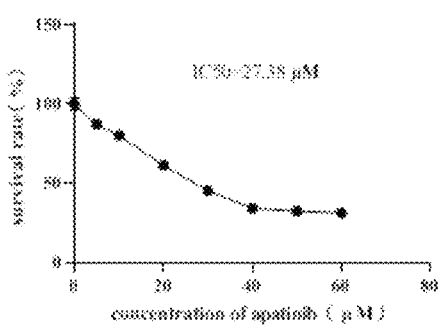
Fig 4-e-3
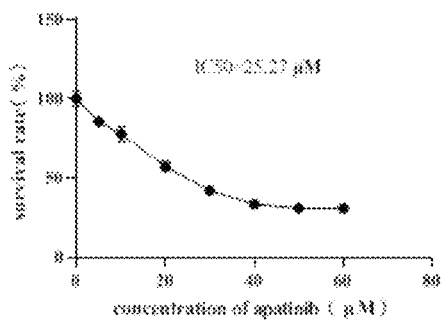
Fig 4-e-4

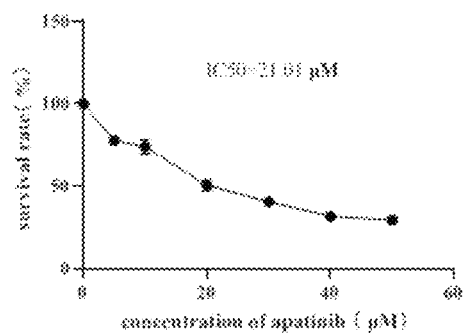
Fig 4-e-5
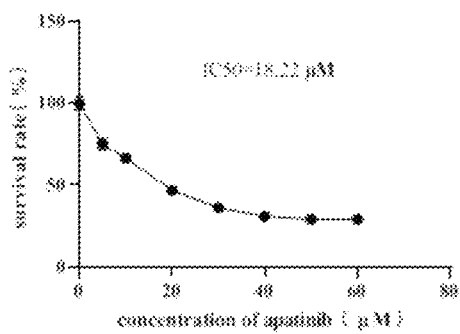
Fig 4-e-6
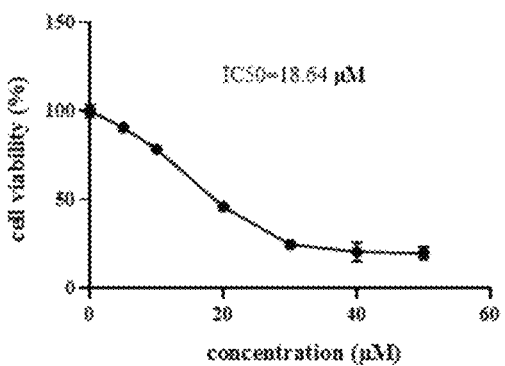
Fig 4-f-1
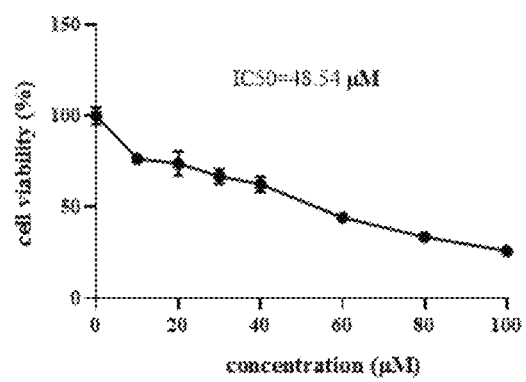
Fig 4-f-2
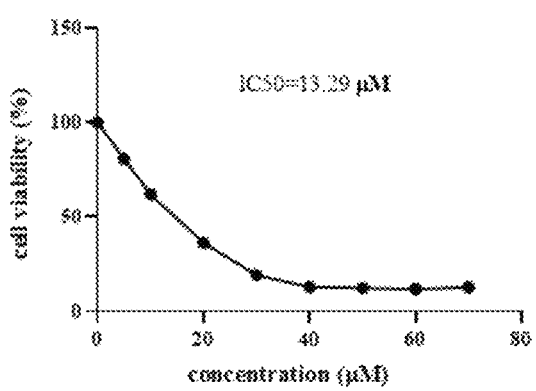
Fig 4-f-3
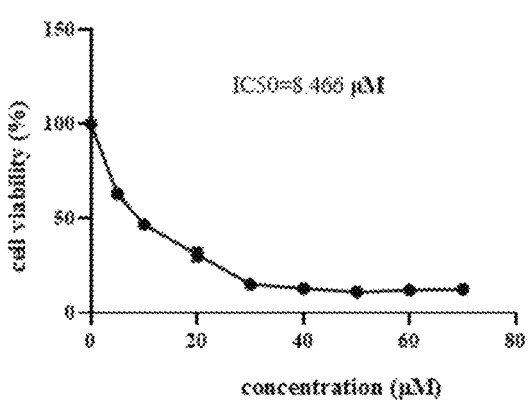
Fig 4-f-4

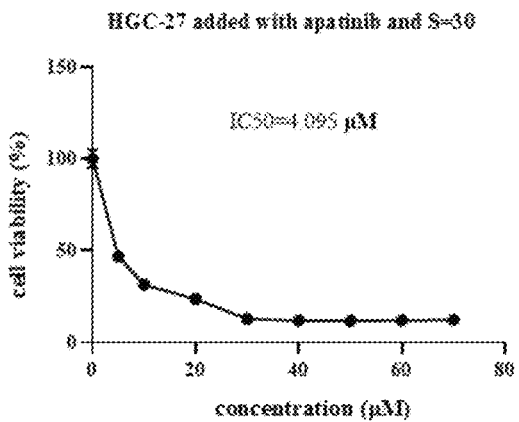
Fig 4-f-5
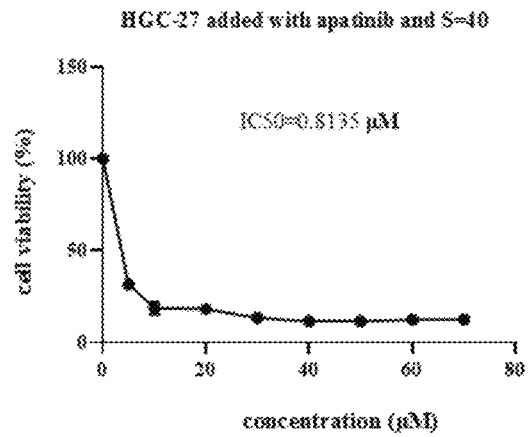
Fig 4-f-6
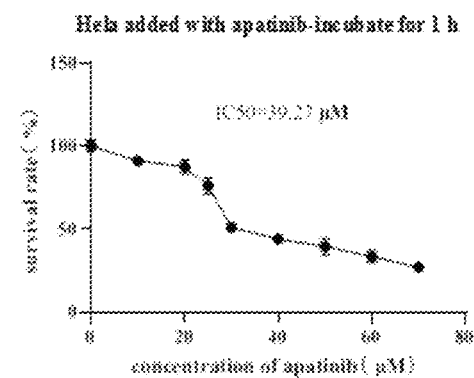
Fig 4-g-1
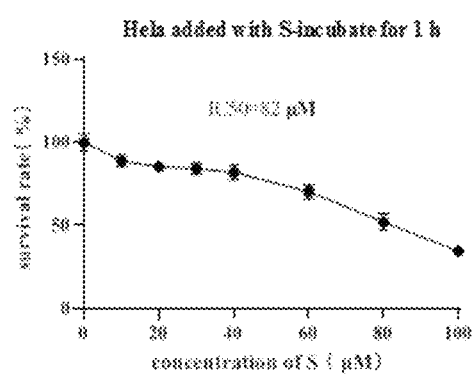
Fig 4-g-2
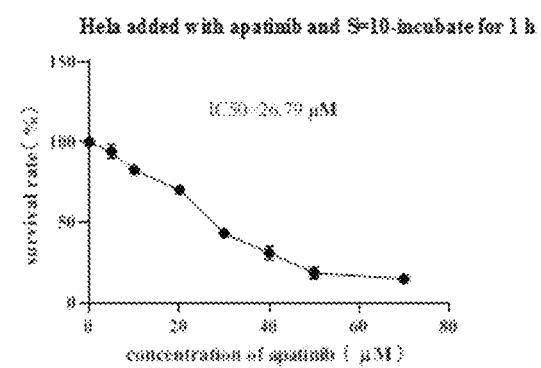
Fig 4-g-3
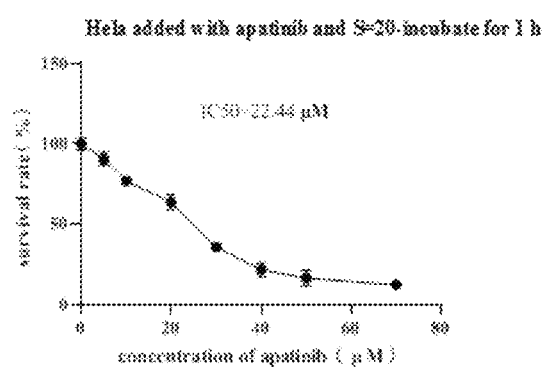
Fig 4-g-4

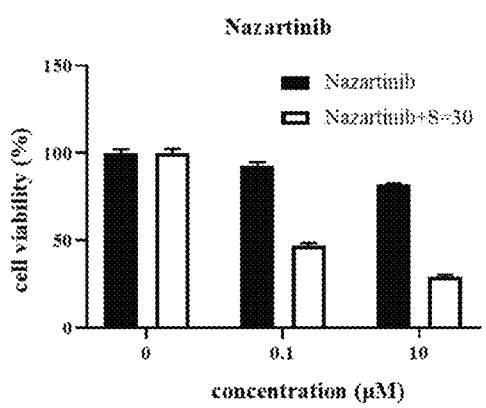
Fig 6-41
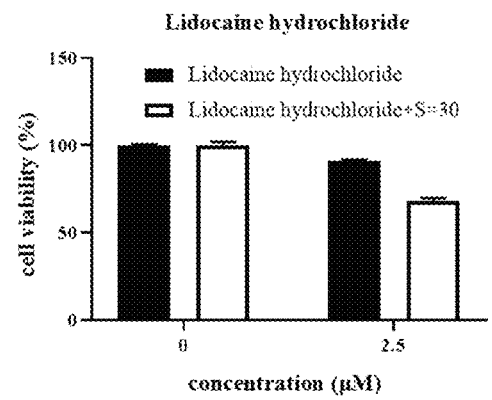
Fig 6-42
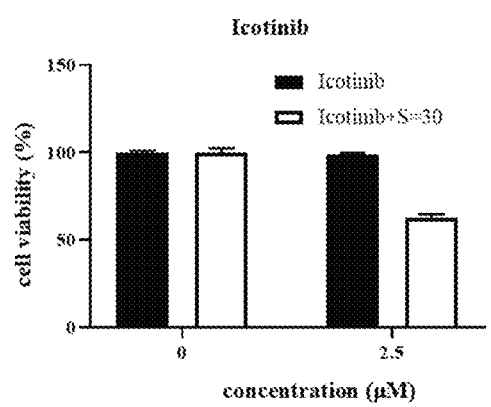
Fig 6-43
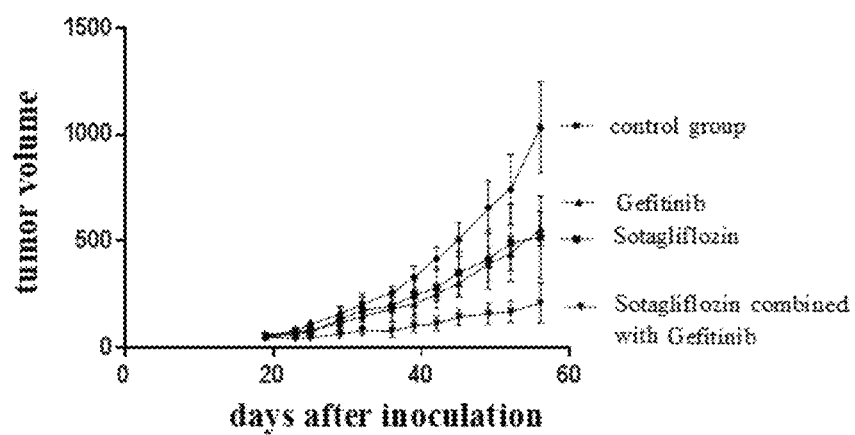
Fig 7-a

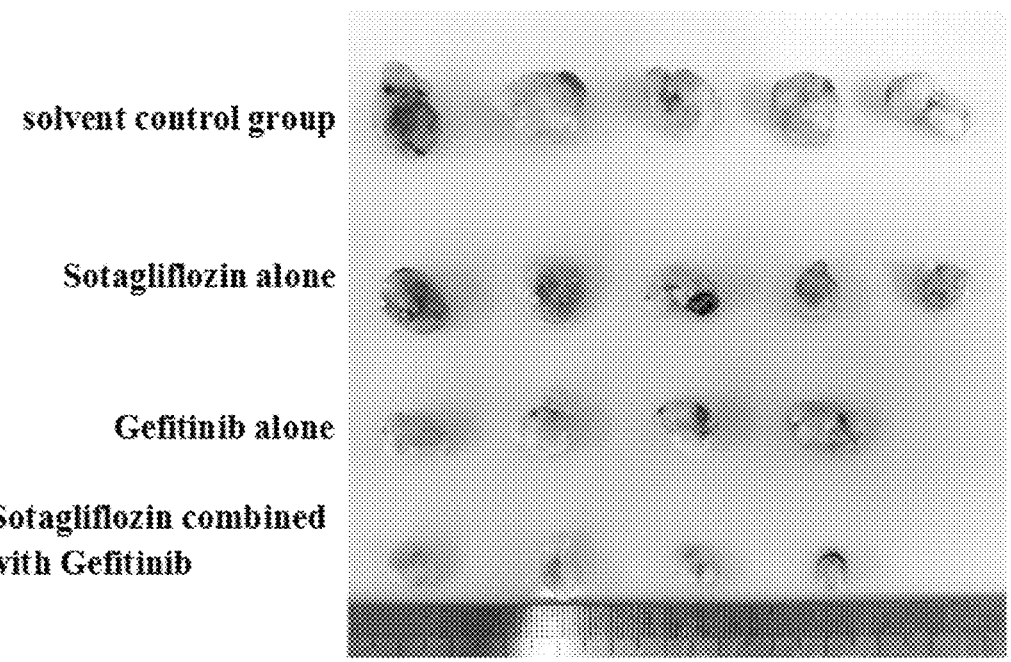
Fig 7-b
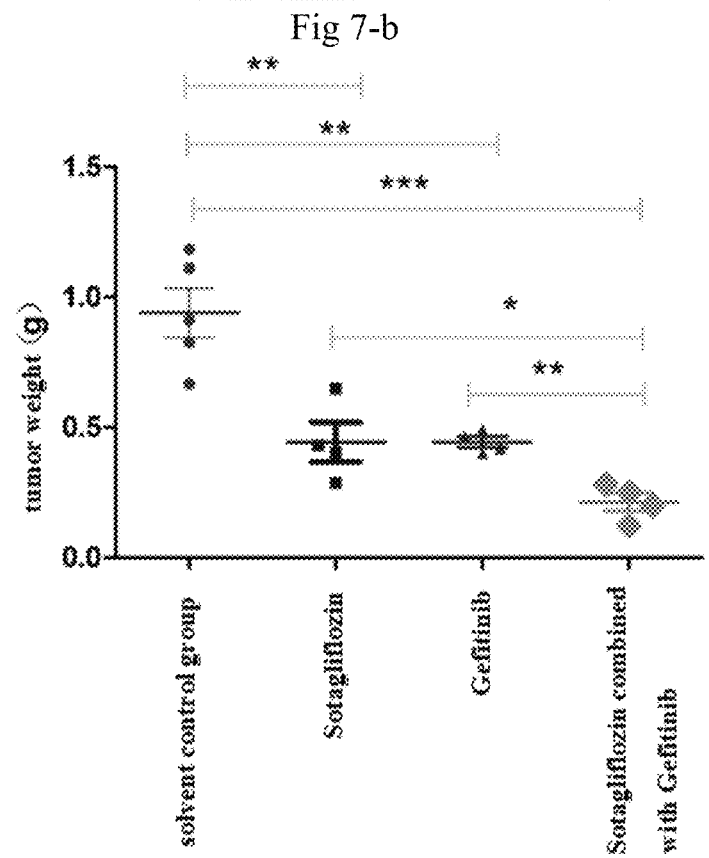
Fig 7-c

COMPOSITION AND USE THEREOF IN THE MANUFACTURE OF MEDICAMENT FOR TREATING CANCER

CROSS REFERENCE TO RELATED APPLICATIONS

This application is a national phase application under 35 U.S.C. § 371 of International Application No. PCT/CN2020/109969, filed Aug. 19, 2020, which claims the priority of Chinese Patent Application No. 202010643576.5 filed at the Chinese Patent Office on Jul. 6, 2020, titled "COMPOSITION AND USE THEREOF IN THE MANUFACTURE OF MEDICAMENT FOR TREATING CANCER", the entire content of each of which is incorporated herein by reference.

FIELD

The present invention relates to the field of medicine technology, and in particular to a composition and the use thereof in the manufacture of a medicament for treating cancer.

BACKGROUND

1. Cancer Epidemiology

Non-communicable diseases are the main cause of death in the world, and cancer is the disease with the highest fatality rate among non-communicable diseases, bringing a heavy burden to the social health and medical system. Traditional cancer treatment is mainly surgery, radiotherapy and chemotherapy, and chemotherapy is the main treatment for advanced cancer. Classical chemotherapy has serious side effects due to poor targeting. The emergence of targeted chemotherapy drug such as Gleevec has greatly reduced the pain caused by chemotherapy to patients. Targeted drugs are designed based on the different growth characteristics and expression of cancer cells compared with normal cells. For example, Gleevec specifically targets the constitutively activated tyrosine kinases in chronic myelogenous leukemia to achieve a good therapeutic effect (Flynn and Gerriets, 2020). Another distinguishing feature of cancer cells compared with normal cells is the change in metabolism. In order to meet the needs of cell components for rapid proliferation and maintain the energy supply needed for survival, cancer cells prefer to use glucose by aerobic glycolysis, which is called the Warburg effect (Warburg, 1956). Aerobic glycolysis cannot fully oxidize glucose to produce ATP, but can produce a large amount of intermediate metabolites for DNA and protein synthesis to promote cancer cell proliferation. Therefore, it is feasible to target the sugar metabolism of tumor cells to inhibit the proliferation of cancer cells (Kroemer and Pouyssegur, 2008).

2. Sotagliflozin and Cancer Treatment

Cancer cells absorb glucose from the external environment mainly through glucose transporters. Glucose transporters are divided into two major families, one of which is the GLUT family that transports glucose along the glucose concentration gradient by assisting diffusion, and the other is the sodium-glucose co-transporter SGLT family that co-transports sodium ions for glucose absorption and actively transports glucose from the external for cell consumption by consuming ATP (Navale and Paranjape, 2016). The two main members of the SGLT family are SGLT1 and SGLT2. SGLT2 is mainly distributed at the front end of the proximal convoluted tubule of the kidney, and reabsorbs more than 97% of the glucose in the original urine into the blood through active transport, while SGLT1 is mainly distributed in the epithelial cells of the small intestine chorion and the distal end of the proximal convoluted tubules of the kidney, and through active transport absorbs glucose from food in the intestine and the remaining 3% glucose in the original urine after the absorption by SGLT2 (Dominguez Rieg and Rieg, 2019). Due to the important role of SGLT1 and SGLT2 in sugar absorption and reabsorption, they have become ideal targets for diabetes treatment. Currently Empagliflozin, Canagliflozin and Dapagliflozin targeting SGLT2 have shown good therapeutic effects in the treatment of type 2 diabetes, and the effect of reducing cardiovascular disease. Mizagliflozin, which targets SGLT1 alone, has entered the clinical research phase. Sotagliflozin, which targets both SGLT1 and SGLT2, has been approved for marketing in the EU.

3. TKI and Cancer Resistance to TKI

Receptor tyrosine kinase (RTK) is the most common gene that promotes cancer development in cancer. After binding to the corresponding ligand, RTK usually dimerizes and then catalyzes autophosphorylation and initiates a series of downstream signal cascades to promote cancer cell proliferation (Lemmon and Schlessinger, 2010; Yarden and Pines, 2012). Cancer cells usually overexpress RTK or have mutations that constitutively activate RTK to up-regulate the activity of RTK, to promote the proliferation per se. Therefore, the main means for developing anti-cancer drugs is to target RTK activity, including small molecule tyrosine kinase activity inhibitors (TKI) targeting the ATP binding pocket of RTKs and monoclonal antibodies targeting ligand binding (Thomas and Weihua, 2019). The development of TKI has successfully prolonged the progression-free survival and significantly improved the quality of life of patients with RTK overexpression or constitutive activation. At present, most TKIs are first-line drugs in the corresponding cancer field. However, in addition to cancer patients who are naturally resistant to TKI, patients who respond well to TKI treatment may also develop acquired resistance within a treatment cycle of about one year (Camidge et al.; Cortot and Janne, 2014). The causes of drug resistance are mainly divided into pharmacological resistance and biological resistance. Pharmacological resistance is mostly due to the interaction between the body and the drug, which causes the drug to fail to reach an effective concentration around the cancer cell, although the cancer cell itself may still be sensitive to the drug. Biological resistance is caused by cancer heterogeneity, drug resistance mutations under drug selection pressure, and activation of alternative signaling pathways (Minuti, G., A et al). Biological resistance is the main cause of resistance to TKI drugs. With response to the mechanism of acquired drug resistance in cancer cells, researchers have designed many methods to overcome cancer drug resistance, including the development of second-generation, third-generation and other newer inhibitors against conventional drug-resistant mutations, and the combination with radiotherapy or chemotherapy and with new targeted drugs after drug resistance. At present, even the third-generation inhibitors may lead to acquired resistance, and radiotherapy and chemotherapy have little effect. Therefore, the combination with other targeted drugs to overcome resistance is the first choice.

SUMMARY

In view of this, the technical problem to be solved by the present invention is to provide a composition and the use thereof in the manufacture of a medicament for treating cancer. The composition may comprise Sotagliflozin and a tyrosine kinase activity inhibitor.

The present invention also provides a composition comprising a compound of formula I

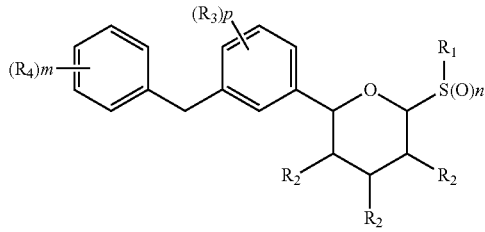

Formula I wherein:
R₁ is hydrogen, or $C_{1-10}$-alkyl, $C_{1-5}$-cycloalkyl or 5-membered heterocyclic ring optionally substituted with one or more $R_{1A}$;
each $R_{1A}$ is independently amino, ester, amide, thiol, carboxylic acid, cyano, halogen, hydroxyl, or $C_{1-4}$-alkoxy, $C_{1-5}$-cycloalkyl or 5-membered heterocyclic ring optionally substituted with one or more $R_{1B}$; each $R_{1B}$ is independently $C_{1-4}$-alkyl, halogen or hydroxy; n is 0, 1 or 2;
each $R_2$ is independently F or $OR_{2A}$, wherein each $R_{2A}$ is independently hydrogen, $C_{1-4}$-alkyl or acyl;
each R3 is independently halogen, hydroxy, or $C_{1-10}$-alkyl or $C_{1-10}$-alkoxy optionally substituted with one or more $R_{3A}$;
each $R_{3A}$ is independently amino, ester, amide, thiol, carboxylic acid, cyano, halogen, hydroxyl, or $C_{1-4}$-alkoxy, $C_{1-5}$-cycloalkyl or 5-membered heterocyclic ring optionally substituted with one or more $R_{3B}$; each $R_{3B}$ is independently $C_{1-4}$-alkyl, amino, cyano, halogen or hydroxyl; p is 0, 1 or 2;
each $R_4$ is independently $R_{4A}$, —$N(R_{4A})(R_{4B})$, —$OR_{4A}$, —$SR_{4A}$, —$S(O)R_{4A}$ or —$S(O)_2R_{4A}$;
$R_{4A}$ is $C_{4-20}$-alkyl or 4-20 membered heteroalkyl optionally substituted with one or more $R_{4C}$ and optionally attached to another $R_{4A}$ to provide a dimer or trimer; $R_{4B}$ is hydrogen or $R_{4A}$; each $R_{4C}$ is independently amino, aminoacyl, azo, carbonyl, carboxyl, cyano, formyl, guanidino, halogen, hydroxyl, iminoacyl, imino, isothiocyanate, nitrile, nitro, nitroso, nitroxyl, oxy, alkylthio, sulfinyl, sulfonyl, thioaldehyde, thiocyanate, thioketone, thiourea, urea or $X_1$, $X_1$-$L_1$-$X_2$ or $X_1$-$L_1$-$X_2$-$L_2$-$X_3$, wherein each of $X_1$, $X_2$ and $X_3$ is independently $C_{1-4}$-alkyl, $C_{1-6}$-cycloalkyl, 5- or 6-membered heterocyclic or aryl optionally substituted with one or more $R_{4D}$, and each of $L_1$ and $L_2$ is independently $C_{1-6}$-alkyl or 1-10 membered heteroalkyl optionally substituted with one or more $R_{4E}$; each $R_{4D}$ is independently $R_{4E}$, or $C_{1-6}$-alkyl optionally substituted with one or more $R_{4E}$; each $R_{4E}$ is independently amino, aminoacyl, azo, carbonyl, carboxyl, cyano, formyl, guanidino, halogen, hydroxyl, iminoacyl, imino, isothiocyanate, nitrile, nitro, nitroso, nitroxyl, oxo, alkylthio, sulfinyl, sulfonyl, thioaldehyde, thiocyanate, thioketone or urea; and m is 1, 2 or 3;
or a pharmaceutically acceptable salt, dimer or trimer thereof; and
a tyrosine kinase activity inhibitor.

In an embodiment, R₁ is methyl, n=0; each $R_2$ is —OH; p=1, $R_3$ is Cl; m=1, and $R_4$ is ethoxy.

In some embodiments, the compound of Formula I is Sotagliflozin with the structure as shown in Formula II.

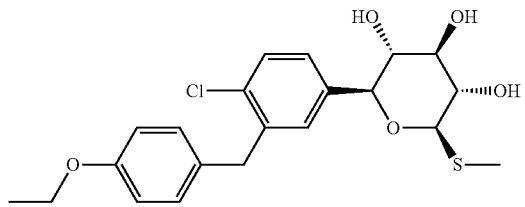

Formula II

In some embodiments, the composition consists of Sotagliflozin and a tyrosine kinase activity inhibitor.

The tyrosine kinase activity inhibitor includes EGFR inhibitor, c-Kit, c-Met, c-Ret, Raf, PDGFR, BTK, PKA/C, FGFR inhibitor and VEGFR inhibitor.

The EGFR inhibitor includes: Gefitinib, Erlotinib, Afatinib, Lapatinib ditosylate, Genistein, Lapatinib, Saputinib, Daphnetin, DacOlmutinib, Varlitinib, Icotinib, Lidocaine hydrochloride, Osimertinib mesylate, Osimertinib, Poziotinib, Nazartinib, AZD3759, Olmutinib, Avitinib, Neratinib, Lazertinib;

The c-Met inhibitor includes Cabozantinib;

The PKA/C inhibitor includes Daphnetin;

The BTK inhibitor includes Olmutinib;

The c-Ret inhibitor includes Regorafenib monohydrate and Regorafenib;

The Raf inhibitor includes Regorafenib monohydrate;

The FGFR inhibitor includes 4-[(1E)-2-[5-[(1R)-1-(3,5-dichloro-4-pyridyl)ethoxy]-1H-indazol-3-yl]vinyl]-1H-pyrazole-1-ethanol(LY2874455), Nintedanib, Nintedanib ethanesulfonate, Ponatinib, Brivanib, Brivanib alaninate;

The c-Kit inhibitor includes Axitinib, Pazopanib, Pazopanib HCl, Regorafenib monohydrate, Sunitinib malate, Sunitinib, Sitravatinib, Telatinib;

The PDGFR inhibitor includes Axitinib, Tivozanib, Telatinib, Nintedanib, Nintedanib ethanesulfonate salt, Pazopanib, Pazopanib HCl, Ponatinib;

The VEGFR inhibitors includes Apatinib, Axitinib, Nintedanib, Cediranib, Pazopanib HCl, Sunitinib malate, Brivanib, Cabozantinib, Brivanib Alaninate, Lenvatinib, Regorafenib, ENMD-2076, ENMD-2076 L-(+)-tartaric acid, Tivozanib, Ponatinib, Fruquintinib, Telatinib, Taxifolin, Pazopanib, Cabozantinib malate, Vitamin E, Regorafenib monohydrate, Nintedanib ethanesulfonate salt, Lenvatinib mesylate, Cediranib maleate, LY2874455, Sunitinib, Sitravatinib, Anlotinib, Sorafenib, Vandetanib and Bevacizumab and other monoclonal antibodies targeting VEGFR.

In the present disclosure, the anti-tumor drugs used to verify the efficacy of Sotagliflozin in combination with the anti-tumor drugs include: ENMD-2076, Tivozanib, Genistein, Ponatinib, Daphnetin, DacOlmutinib, Varlitinib, Icotinib, Osimertinib mesylate, Osimertinib, Nazartinib, AZD3759, Anlotinib, Avitinib, Lazertinib, Lidocaine hydrochloride, Y2874455, Axitinib, Nintedanib, Cediranib, Pazopanib HCl, Sunitinib malate, Brivanib, Cabozantinib, Brivanib Alaninate, Lenvatinib, Regorafenib, ENMD-2076 L-(+)-Tartaric acid, Telatinib, Pazopanib, Cabozantinib malate, Regorafenib monohydrate, Nintedanib ethanesulfonate salt, Lenvatinib mesylate, Cediranib maleate, Fruquintinib, Sunitinib, Olmutinib, Sitravatinib, Vandetanib, Gefitinib, Afatinib, Apatinib, Erlotinib, Sorafenib, Taxifolin or Vitamin E.

The molar ratio of the compound of formula I or a pharmaceutically acceptable salt, dimer or trimer thereof to the tyrosine kinase activity inhibitor is (10~40):(5~60).

In some embodiments, the molar ratio of Sotagliflozin to the tyrosine kinase activity inhibitor is (10~40):(5~60).

The present disclosure provides use of the composition of the present disclosure in the manufacture of a medicament for treating cancer.

The cancers include: bladder cancer, blood cancer, bone cancer, brain cancer, breast cancer, central nervous system cancer, cervical cancer, colon cancer, endometrial cancer, esophageal cancer, gallbladder cancer, gastrointestinal cancer, external genital cancer, urogenital tract cancer, head cancer, kidney cancer, laryngeal cancer, liver cancer, lung cancer, muscle tissue cancer, neck cancer, oral or nasal mucosal cancer, ovarian cancer, pancreas cancer, prostate cancer, skin cancer, spleen cancer, small bowel cancer, large bowel cancer, stomach cancer, testicular cancer and/or thyroid cancer.

In the present disclosure, the treatment comprises inhibiting tumor cell proliferation and/or inhibiting tumor volume. In the examples of the present disclosure, lung cancer cells, colorectal cancer cells, cervical cancer, ovarian cancer, cholangiocarcinoma, gastric cancer, esophageal cancer, liver cancer cells are used to verify the effect of the combination of the two drugs.

The present disclosure also provides a medicament for the treatment of cancer, comprising the composition of the present disclosure.

The medicament is administered orally, and its dosage forms include granules, pills, powders, tablets, capsules, oral solutions or syrups.

In some embodiments of the present disclosure, the capsule is a hard capsule or a soft capsule.

In some embodiments of the present disclosure, the tablet is an oral tablet or a buccal tablet.

Tablets refer to tablets for oral administration, and the active ingredients in most of such tablets are absorbed through the gastrointestinal tract to exert their effects, and active ingredients in some tablets act locally in the gastrointestinal tract. In some embodiments of the present disclosure, the tablets are ordinary compressed tablets, dispersible tablets, effervescent tablets, chewable tablets, coated tablets or sustained and controlled release tablets.

The medicament also comprises pharmaceutically acceptable auxiliary materials, including one or more of fruit powder, edible essence, sweetener, sour agent, filler, lubricant, preservative, suspending agent, food coloring, diluent, emulsifier, disintegrant or plasticizer.

The present disclosure also provides a method for treating cancer, comprising administering the medicament of the present disclosure.

The present disclosure provides a composition containing a compound of formula I or a pharmaceutically acceptable salt, dimer or trimer thereof, and a tyrosine kinase activity inhibitor. The present disclosure shows through in vivo and in vitro anti-tumor tests that, based on the inhibitory effect of the tyrosine kinase activity inhibitor targeting VEGFR, EGFR and other receptor tyrosine kinases, the combination of Sotagliflozin and a tyrosine kinase activity inhibitor may exhibit a synergistic inhibitory effect on tumors, and the efficacy of the combination is significantly better than that of the single drug.

BRIEF DESCRIPTION OF DRAWINGS

FIG. 2-*a*-2 shows the inhibitory effect of different concentrations of Sotagliflozin on lung cancer cell line A549; FIG. 2-*a*-3 shows the inhibitory effect of different concentrations of Gefitinib+10 µM Sotagliflozin on lung cancer cell line A549 in test group 1;

FIG. 2-*a*-4 shows the effects of different concentrations of Gefitinib+20 µM Sotagliflozin on lung cancer cell line A549 in test group 2; FIG. 2-*a*-5 shows the inhibitory effect of different concentrations of Gefitinib+30 µM Sotagliflozin on lung cancer cell line A549 in test group 3;

FIG. 2-*b* shows the inhibition rate of Gefitinib alone and the combination of Sotagliflozin and Gefitinib on the growth of colorectal cancer cell line LoVo;

FIG. 2-*c* shows the inhibition rate of Gefitinib alone and the combination of Sotagliflozin and Gefitinib on the growth of colorectal cancer cell line HT29;

FIG. 2-*d* shows the inhibition rate of Gefitinib alone and the combination of Sotagliflozin and Gefitinib on the growth of colorectal cancer cell line SW620;

FIG. 2-*e* shows the inhibition rate of Gefitinib alone and the combination of Sotagliflozin and Gefitinib on the growth of colorectal cancer cell line HCT116;

FIG. 2-*f*-1 shows the inhibition rate of different concentrations of Gefitinib alone on the growth of ovarian cancer cell line SKOV3; FIG. 2-*f*-2 shows the inhibitory rate of different concentrations of Sotagliflozin on ovarian cancer cell line SKOV3; FIG. 2-*f*-3 shows the inhibition rate of 10 µmol/L Sotagliflozin with different concentrations of Gefitinib on the growth of ovarian cancer cell line SKOV3; FIG. 2-*f*-4 shows the inhibition rate of 20 µmol/L Sotagliflozin with different concentrations of Gefitinib on the growth of ovarian cancer cell line SKOV3; FIG. 2-*f*-5 shows the inhibition rate of 30 µmol/L Sotagliflozin with different concentrations of Gefitinib on the growth of ovarian cancer cell line SKOV3; and FIG. 2-*f*-6 shows the inhibition rate of 40 µmol/L Sotagliflozin with different concentrations of Gefitinib on the growth of ovarian cancer cell line SKOV3;

FIG. 2-*g*-1 shows the inhibition rate of different concentrations of Gefitinib alone on the growth of esophageal cancer cell line KYSE30; FIG. 2-*g*-2 shows the inhibitory rate of different concentrations of Sotagliflozin on esophageal cancer cell line KYSE30; FIG. 2-*g*-3 shows the inhibition rate of 10 µmol/L Sotagliflozin with different concentrations of Gefitinib on the growth of esophageal cancer cell line KYSE30; FIG. 2-*g*-4 shows the inhibition rate of 20 µmol/L Sotagliflozin with different concentrations of Gefitinib on the growth of esophageal cancer cell line KYSE30; FIG. 2-*g*-5 shows the inhibition rate of 30 µmol/L Sotagliflozin with different concentrations of Gefitinib on the growth of esophageal cancer cell line KYSE30; and FIG. 2-*g*-6 shows the inhibition rate of 40 µmol/L Sotagliflozin with different concentrations of Gefitinib on the growth of esophageal cancer cell line KYSE30;

FIG. 2-*h*-1 shows the inhibition rate of different concentrations of Gefitinib alone on the growth of gastric cancer cell line HGC-27; FIG. 2-*h*-2 shows the inhibition rate of different concentrations of Sotagliflozin on gastric cancer cell line HGC-27; FIG. 2-*h*-3 shows the inhibition rate of 10 μmol/L Sotagliflozin with different concentrations of Gefitinib on the growth of gastric cancer cell line HGC-27; FIG. 2-*h*-4 shows the inhibition rate of 20 μmol/L Sotagliflozin with different concentrations of Gefitinib on the growth of gastric cancer cell line HGC-27; FIG. 2-*h*-5 shows the inhibition rate of 30 μmol/L Sotagliflozin with different concentrations of Gefitinib on the growth of gastric cancer cell line HGC-27; and FIG. 2-*h*-6 shows the inhibition rate of 40 μmol/L Sotagliflozin with different concentrations of Gefitinib on the growth of gastric cancer cell line HGC-27;

FIG. 2-*i*-1 shows the inhibition effect of different concentrations of Gefitinib alone on the growth of cervical cancer cell line HeLa; FIG. 2-*i*-2 shows the inhibitory effect of different concentrations of Sotagliflozin on cervical cancer cell line HeLa; FIG. 2-*i*-3 shows the inhibition effect of 10 μmol/L Sotagliflozin with different concentrations of Gefitinib on the growth of cervical cancer cell line HeLa; FIG. 2-*i*-4 shows the inhibition effect of 20 μmol/L Sotagliflozin with different concentrations of Gefitinib on the growth of cervical cancer cell line HeLa; FIG. 2-*i*-5 shows the inhibition effect of 30 μmol/L Sotagliflozin with different concentrations of Gefitinib on the growth of cervical cancer cell line HeLa; and FIG. 2-*i*-6 shows the inhibition effect of 40 μmol/L Sotagliflozin with different concentrations of Gefitinib on the growth of cervical cancer cell line HeLa;

FIG. 2-*j*-1 shows the inhibition effect of different concentrations of Gefitinib alone on the growth of cholangiocarcinoma cell line RBE; FIG. 2-*j*-2 shows the inhibitory effect of different concentrations of Sotagliflozin on cholangiocarcinoma cell line RBE; FIG. 2-*j*-3 shows the inhibition effect of 10 μmol/L Sotagliflozin with different concentrations of Gefitinib on the growth of cholangiocarcinoma cell line RBE; FIG. 2-*j*-4 shows the inhibition effect of 20 μmol/L Sotagliflozin with different concentrations of Gefitinib on the growth of cholangiocarcinoma cell line RBE; FIG. 2-*j*-5 shows the inhibition effect of 30 μmol/L Sotagliflozin with different concentrations of Gefitinib on the growth of cholangiocarcinoma cell line RBE; and FIG. 2-*j*-6 shows the inhibition effect of 40 μmol/L Sotagliflozin with different concentrations of Gefitinib on the growth of cholangiocarcinoma cell line RBE;

FIG. 2-*k*-1 shows the inhibitory effect of different concentrations of Afatinib on lung cancer cell line A549; FIG. 2-*k*-2 shows the inhibitory effect of different concentrations of Sotagliflozin on lung cancer cell line A549; FIG. 2-*k*-3 shows the inhibitory effect of different concentrations of Afatinib+10 μM Sotagliflozin on lung cancer cell line A549 in test group 1; FIG. 2-*k*-4 shows the inhibitory effect of different concentrations of Afatinib+20 μM Sotagliflozin on lung cancer cell line A549 in test group 2; FIG. 2-*k*-5 shows the inhibitory effect of different concentrations of Afatinib+30 μM Sotagliflozin on lung cancer cell line A549 in test group 3; and FIG. 2-*k*-6 shows the inhibitory effect of different concentrations of Afatinib+40 μM Sotagliflozin on lung cancer cell line A549 in test group 4;

FIG. 2-*l*-1 shows the inhibitory effect of different concentrations of Erlotinib on lung cancer cell line A549; FIG. 2-*l*-2 shows the inhibitory effect of different concentrations of Sotagliflozin on lung cancer cell line A549; FIG. 2-*l*-3 shows the inhibitory effect of different concentrations of Erlotinib+10 μM Sotagliflozin on lung cancer cell line A549 in test group 1; FIG. 2-*l*-4 shows the inhibitory effect of different concentrations of Erlotinib+20 μM Sotagliflozin on lung cancer cell line A549 in test group 2; FIG. 2-*l*-5 shows the inhibitory effect of different concentrations of Erlotinib+30 μM Sotagliflozin on lung cancer cell line A549 in test group 3; and FIG. 2-*l*-6 shows the inhibitory effect of different concentrations of Erlotinib+40 μM Sotagliflozin on lung cancer cell line A549 in test group 4;

FIG. 4-*a*-2 shows the inhibition effect of Apatinib alone and the combination of Sotagliflozin and Apatinib on the growth of colorectal cancer cell line LoVo;

FIG. 4-*a*-3 shows the inhibition effect of Apatinib alone and the combination of Sotagliflozin and Apatinib on the growth of colorectal cancer cell line HT29;

FIG. 4-*a*-4 shows the inhibition effect of Apatinib alone and the combination of Sotagliflozin and Apatinib on the growth of colorectal cancer cell line SW620;

FIG. 4-*a*-5 shows the inhibition effect of Apatinib alone and the combination of Sotagliflozin and Apatinib on the growth of colorectal cancer cell line SW480;

FIG. 4-*b*-1 shows the inhibition effect of different concentrations of Apatinib on cell line HepG2;

FIG. 4-*b*-2 shows the inhibition effect of different concentrations of Sotagliflozin on cell line HepG2;

FIG. 4-*b*-3 shows the inhibition effect of the drug combination of different concentrations of Apatinib+10 μM Sotagliflozin on cell line HepG2 in test group 1;

FIG. 4-*b*-4 shows the inhibition effect of the drug combination of different concentrations of Apatinib+20 μM Sotagliflozin on cell line HepG2 in test group 2;

FIG. 4-*b*-5 shows the inhibition effect of the drug combination of different concentrations of Apatinib+30 μM Sotagliflozin on cell line HepG2 in test group 3;

FIG. 4-*b*-6 shows the inhibition effect of the drug combination of different concentrations of Apatinib+40 μM Sotagliflozin on cell line HepG2 in test group 4;

FIG. 4-*c*-1 shows the inhibition effect of different concentrations of Apatinib alone on the growth of cholangiocarcinoma cell line RBE; FIG. 4-*c*-2 shows the inhibition effect of different concentrations of Sotagliflozin alone on the growth of cholangiocarcinoma cell line RBE; FIG. 4-*c*-3 shows the inhibition effect of 10 μmol/L Sotagliflozin with different concentrations of Apatinib on the growth of cholangiocarcinoma cell line RBE; FIG. 4-*c*-4 shows the inhibition effect of 20 μmol/L Sotagliflozin with different concentrations of Apatinib on the growth of cell line RBE; FIG. 4-*c*-5 shows the inhibition effect of 30 μmol/L Sotagliflozin with different concentrations of Apatinib on the growth of cholangiocarcinoma cell line RBE; FIG. 4-*c*-6 shows the inhibition effect of 40 μmol/L Sotagliflozin with different concentrations of Apatinib on the growth of cholangiocarcinoma cell line RBE;

FIG. 4-*d*-1 shows the inhibition effect of different concentrations of Apatinib alone on the growth of esophageal cancer cell line KYSE30; FIG. 4-*d*-2 shows the inhibition effect of different concentrations of Sotagliflozin alone on the growth of esophageal cancer cell line KYSE30; FIG. 4-*d*-3 shows the inhibition effect of 10 μmol/L Sotagliflozin with different concentrations of Apatinib on the growth of esophageal cancer cell line KYSE30; FIG. 4-*d*-4 shows the inhibition effect of 20 μmol/L Sotagliflozin with different concentrations of Apatinib on the growth of esophageal cancer cell line KYSE30; FIG. 4-*d*-5 shows the inhibition effect of 30 μmol/L Sotagliflozin with different concentrations of Apatinib on the growth of esophageal cancer cell line KYSE30; FIG. 4-d-6 shows the inhibition effect of 40 μmol/L Sotagliflozin with different concentrations of Apatinib on the growth of esophageal cancer cell line KYSE30;

FIG. 4-e-1 shows the inhibition effect of different concentrations of Apatinib alone on the growth of ovarian cancer cell line SKOV3; FIG. 4-e-2 shows the inhibition effect of different concentrations of Sotagliflozin alone on the growth of ovarian cancer cell line SKOV3; FIG. 4-e-3 shows the inhibition effect of 10 μmol/L Sotagliflozin with different concentrations of Apatinib on the growth of ovarian cancer cell line SKOV3; FIG. 4-e-4 shows the inhibition effect of 20 μmol/L Sotagliflozin with different concentrations of Apatinib on the growth of ovarian cancer cell line SKOV3; FIG. 4-e-5 shows the inhibition effect of 30 μmol/L Sotagliflozin with different concentrations of Apatinib on the growth of ovarian cancer cell line SKOV3; FIG. 4-e-6 shows the inhibition effect of 40 μmol/L Sotagliflozin with different concentrations of Apatinib on the growth of ovarian cancer cell line SKOV3;

FIG. 4-f-1 shows the inhibition effect of different concentrations of Apatinib alone on the growth of gastric cancer cell line NGC-27; FIG. 4-f-2 shows the inhibition effect of different concentrations of Sotagliflozin alone on the growth of gastric cancer cell line NGC-27; FIG. 4-f-3 shows the inhibition effect of 10 μmol/L Sotagliflozin with different concentrations of Apatinib on the growth of gastric cancer cell line NGC-27; FIG. 4-f-4 shows the inhibition effect of 20 μmol/L Sotagliflozin with different concentrations of Apatinib on the growth of gastric cancer cell line NGC-27; FIG. 4-f-5 shows the inhibition effect of 30 μmol/L Sotagliflozin with different concentrations of Apatinib on the growth of gastric cancer cell line NGC-27; FIG. 4-f-6 shows the inhibition effect of 40 μmol/L Sotagliflozin with different concentrations of Apatinib on the growth of gastric cancer cell line NGC-27;

FIG. 4-g-1 shows the inhibition effect of different concentrations of Apatinib alone on the growth of cervical cancer cell line HeLa; FIG. 4-g-2 shows the inhibition effect of different concentrations of Sotagliflozin alone on the growth of cervical cancer cell line HeLa; FIG. 4-g-3 shows the inhibition effect of 10 μmol/L Sotagliflozin with different concentrations of Apatinib on the growth of cervical cancer cell line HeLa; FIG. 4-g-4 shows the inhibition effect of 20 μmol/L Sotagliflozin with different concentrations of Apatinib on the growth of cervical cancer cell line HeLa; FIG. 4-g-5 shows the inhibition effect of 30 μmol/L Sotagliflozin with different concentrations of Apatinib on the growth of cervical cancer cell line HeLa; FIG. 4-g-6 shows the inhibition effect of 40 μmol/L Sotagliflozin with different concentrations of Apatinib on the growth of cervical cancer cell line HeLa;

FIG. 6-1 to FIG. 6-43 show the combination effect of Sotagliflozin combined with Axitinib (FIG. 6-1), Nintedanib (FIG. 6-2), Cediranib (FIG. 6-3), Pazopanib HCl (FIG. 6-4), Sunitinib malate (FIG. 6-5), Brivanib (FIG. 6-6), Cabozantinib (FIG. 6-7), Brivanib alaninate (FIG. 6-8), Lenvatinib (FIG. 6-9), Regorafenib (FIG. 6-10), ENMD-2076 (FIG. 6-11), Tivozanib (FIG. 6-12), Ponatinib (FIG. 6-13), ENMD-2076 L-(+)-tartaric acid (FIG. 6-14), Telatinib (FIG. 6-15), Taxifolin (FIG. 6-16), Pazopanib (FIG. 6-17), Cabozantinib malate (FIG. 6-18), Vitamin E (FIG. 6-19), Regorafenib monohydrate (FIG. 6-20), Nintedanib ethanesulfonate salt (FIG. 6-21), Lenvatinib mesylate (FIG. 6-22), Cediranib maleate (FIG. 6-23), LY2874455 (FIG. 6-24), Sunitinib (FIG. 6-25), Sitravatinib (FIG. 6-26), Anlotinib (FIG. 6-27), Sorafenib (FIG. 6-28), Vandetanib (FIG. 6-29), Fruquintinib (FIG. 6-30), Olmutinib (FIG. 6-31), Osimertinib (FIG. 6-32), Genistein (FIG. 6-33), Avitinib (FIG. 6-34), DacOlmutinib (6-35), Osimertinib mesylate (FIG. 6-36), Daphnetin (FIG. 6-37), Varlitinib (FIG. 6-38), AZD3759 (FIG. 6-39), Lazertinib (FIG. 6-40), Nazartinib (FIG. 6-41), Lidocaine hydrochloride (FIG. 6-42), and Icotinib (FIG. 6-43), respectively;

FIG. 7-a shows the growth curve of tumor volume in the tumor-bearing mice modeled by lung cancer A549 cells during the administration of Sotagliflozin alone, Apatinib alone, and the combination of Sotagliflozin and Apatinib;

FIG. 7-b shows the macroscopic view of tumor of the tumor-bearing mice modeled by lung cancer A549 cells after the administration of Sotagliflozin alone, Gefitinib alone, and the combination of Sotagliflozin and Gefitinib:

FIG. 7-c shows the weight of mouse tumors after the administration of Sotagliflozin alone, Gefitinib alone and the combination of Sotagliflozin and Gefitinib.

DETAILED DESCRIPTION

The present disclosure provides a composition and the use thereof in the manufacture of a medicament for treating cancer. Those skilled in the art can learn from the content of the present disclosure and appropriately improve the process parameters. It should be particularly pointed out that all similar replacements and modifications are obvious to those skilled in the art, and are all deemed to be included in the present disclosure. The method and application of the present disclosure have been described through the preferred examples. Those skilled in the art can make changes or appropriate modifications and combinations to the methods and applications described herein without departing from the content, spirit and scope of the present disclosure, to implement and apply the technology of the present disclosure.

Unless specifically stated otherwise in the present disclosure, all technical and scientific terms involved in the present disclosure have the same meanings as commonly understood by those in the art. The technology used in the present disclosure is intended to refer to the technology generally understood in the art, including changes or equivalent replacements of the technology obvious to those skilled in the art. Although it is believed that the following terms are well understood by those skilled in the art, the following definitions are provided to better explain the present disclosure.

As used herein, the terms "including", "comprising", "having", "containing" or "involving" and other variants thereof herein are inclusive or open-ended, and do not exclude other non-listed elements or method steps.

Figures 1, 2, 3:
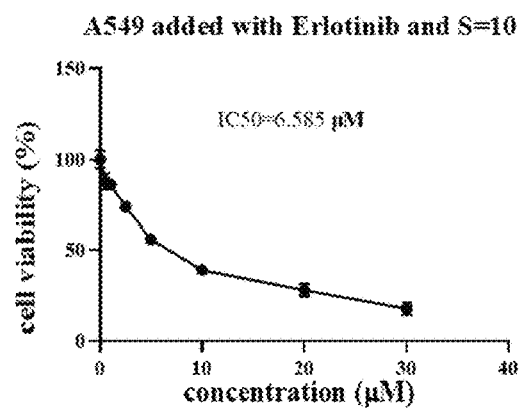
FIG. 1 shows the killing effect of Gefitinib on lung cancer A549 cells cultured in sugar-free medium and sugar-containing medium.
FIG. 2-*a*-1 shows the inhibitory effect of different concentrations of Gefitinib on lung cancer cell line A549.
FIG. 3 shows the killing effect of Gefitinib, Sotagliflozin and the combination thereof on the Gefitinib resistant cell line A549 obtained after screening.

The inventors found in the previous studies that tumor cells in low-sugar medium exhibited reduced proliferation rate and increased sensitivity to TKI inhibitors such as Gefitinib and Apatinib. A549 cells were grown to 80% density, passed, resuspended in a normal medium (25 mM glucose) to a concentration of $4\times10^5$ cells per ml, and plated in a 24-well plate with 1 ml per well. After 24 hours, the medium was changed to sugar-free medium (0 mM glucose) and normal medium, respectively, and added with Gefitinib for treating the cell. After 48 hours, the medium was discarded, and 1 ml of 1×PBS was added to wash once, and 1 ml of 1×Trypan Blue was added to each well for staining for 10 minutes. Then, the trypan blue staining solution was aspirated, and the plate was washed three times by adding 1 ml of 1×PBS, and photographed under a light microscope. The results are shown in FIG. 1. The A549 cells cultured in the sugar-free medium (0 mM glucose) are almost all colored blue, indicating dead cells, while the A549 cells in the normal medium (25 mM glucose) had almost no blue coloration. It shows that the sugar-free environment increases the sensitivity of A549 cells to Gefitinib. At the same time, the lower cell density in the sugar-free medium shows that sugar-free culture can also inhibit the proliferation of cancer cells. According to the background section, cancer cells mainly rely on the SGLT family of proteins to absorb sugar. Therefore, the present disclosure relates use of a composition comprising dual inhibitor Sotagliflozin of SGLT1 and SGLT2, the two most important members of the SGLT family highly expressed in cancer cells, and a tyrosine kinase inhibitor in the manufacture of a medicament for treating cancer.

The term "treatment" as used herein means that after administration of the drug of the present disclosure, the experimental animal suffering from a disease or condition shows partial or full relief of the symptoms, or the symptoms do not continue to worsen after treatment. Therefore, treatment includes cure.

As used herein, "therapeutic effect" refers to the effect caused by the treatment, which is manifested as cell growth inhibition rate or cell death rate at the cellular level, and change, generally reduction or improvement of symptoms of a disease or condition, or cure of a disease or condition at the animal level. In the present disclosure, a medicament is effective if the tumor growth inhibition rate is greater than 60%, and the p-value showing the statistical difference between the tumor volume or weight of the treatment group and the control group is less than 0.05, after the administration of the medicament.

As used herein, "cell growth inhibition rate" refers to the ratio of the average value of the absorbance of the cells stained with MTT in the treatment group to the average value of the absorbance in the control group after drug treatment. "Tumor growth inhibition rate" represents the ratio of the average tumor volume or weight of the treatment group to the average volume or weight of the control group after drug treatment.

In an embodiment, Sotagliflozin is used to treat cancer in a subject.

The term "cancer" as used herein refers to the malignant proliferation of epithelial cells due to changes in genetic material. The cancers includes bladder cancer, blood cancer, bone cancer, brain cancer, breast cancer, central nervous system cancer, cervical cancer, colon cancer, endometrial cancer, esophageal cancer, gallbladder cancer, gastrointestinal cancer, external genital cancer, urogenital tract cancer, head cancer, kidney cancer, laryngeal cancer, liver cancer, lung cancer, muscle tissue cancer, neck cancer, oral or nasal mucosal cancer, ovarian cancer, pancreas cancer, prostate cancer, skin cancer, spleen cancer, small bowel cancer, large bowel cancer, stomach cancer, testicular cancer and/or thyroid cancer.

The invention also relates to a combination of Sotagliflozin and other TKI drugs for the treatment of cancer. In an embodiment, the present disclosure provides use of Sotagliflozin in the manufacture of a medicament for treating cancer in a subject, wherein Sotagliflozin is used in combination with a tyrosine kinase inhibitor for treating cancer.

The term "TKI drug" as used herein includes drugs known in the art for treating cancer, including at least one of EGFR inhibitor, c-Kit, c-Met, c-Ret, Raf, PDGFR, BTK, PKA/C, FGFR inhibitor and VEGFR inhibitor.

The composition provided by the present disclosure comprises Sotagliflozin and a TKI drug.

In an embodiment, the composition consists of Sotagliflozin and Gefitinib in a molar ratio of (10-30):(10-60). Specifically, the molar ratio of Sotagliflozin and Gefitinib is 10:10, 10:20, 10:30, 10:50, 10:60, 20:10, 20:20, 20:30, 20:50, 20:60, 30:10, 30:20, 30:30, 30:50 or 30:60.

In an embodiment, the composition consists of Sotagliflozin and Apatinib in a molar ratio of is (10-40):(5-40). Specifically, the molar ratio of Sotagliflozin and Apatinib may be 10:5, 10:10, 10:20, 10:30, 10:40, 20:5, 20:10, 20:20, 20:30, 20:40, 30:5, 30:10, 30:20, 30:30, 30:40, 40:5, 40:10, 40:20, 40:30, 40:40; alternatively, the molar ratio of Sotagliflozin and Apatinib is (10~40):(5~60). Specifically, the molar ratio of Sotagliflozin and Apatinib is 10:5, 10:10, 10:20, 10:30, 10:40, 10:60, 20:5, 20:10, 20:20, 20:30, 20:40, 20:60, 30:5, 30:10, 30:20, 30:30, 30:40, 30:60, 40:5, 40:10, 40:20, 40:30, 40:40, or 40:60.

In an embodiment, the composition consists of Sotagliflozin and Lenvatinib in a molar ratio of 20:1.

In another embodiment, the composition consists of Sotagliflozin and drug A, and the drug A is at least one of Lapatinib ditosylate, Genistein, Lapatinib, Saputinib, Daphnetin, DacOlmutinib, Varlitinib, Icotinib, Lidocaine hydrochloride, Osimertinib mesylate, Osimertinib, Poziotinib, Nazartinib, AZD3759, Olmutinib, Avitinib, Neratinib, Lazertinib, Axitinib, Nintedanib, Cediranib, Pazopanib HCl, Sunitinib malate, Brivanib, Cabozantinib, Brivanib alaninate, Lenvatinib, Regorafenib, ENMD-2076, ENMD-2076 L-(+)-tartaric acid, Tivozanib, Ponatinib, Fruquintinib, Telatinib, Taxifolin, Pazopanib, Cabozantinib malate, Vitamin E, Regorafenib hydrate, Nintedanib ethanesulfonate salt, Lenvatinib mesylate, Cediranib maleate, LY2874455, Sunitinib, Sitravatinib, Anlotinib, Sorafenib, and Vandetanib.

The reagents and materials used in the present disclosure are all common commercially available products, and all are available in the market.

In the examples of this application, the drugs involved and their Chinese names are shown in Table 1:

TABLE 1

Drugs and their Chinese names

| Chinese name | English name |
| --- | --- |
| 多靶点激酶抑制剂 | ENMD-2076 |
| 替沃扎尼 | Tivozanib |
| 染料木素 | Genistein |
| 帕纳替尼 | Ponatinib |
| 瑞香素 | Daphnetin |
| 达克替尼 | DacOlmutinib |
| 瓦利替尼 | Varlitinib |
| 埃克替尼 | Icotinib |
| 奥斯替尼甲磺酸盐 | Osimertinib mesylate |
| 奥斯替尼 | Osimertinib |
| 那扎替尼 | Nazartinib |
|  | AZD3759 |
| 安罗替尼二氢化物 | Anlotinib (AL3818) dihydrochloride |
| 艾维替尼 | Avitinib |
| 拉泽替尼 | Lazertinib |
| 盐酸利多卡因 | Lidocaine hydrochloride |
| 4-[(1E)-2-[5-[(1R)-1-(3,5-二氯-4-吡啶基乙氧基]-1H-吲唑-3-基乙烯基]-1H-吡唑-1-乙醇 | LY2874455 |

TABLE 1-continued

Drugs and their Chinese names

| Chinese name | English name |
|---|---|
| 阿西替尼 | Axitinib |
| 尼达尼布 | Nintedanib |
| 西地尼布 | Cediranib |
| 盐酸帕唑帕尼 | Pazopanib HCl |
| 苹果酸舒尼替尼 | Sunitinib Malate |
| 布立尼布 | Brivanib |
| 卡博替尼 | Cabozantinib |
| 丙氨酸布立尼布 | Brivanib Alaninate |
| 乐伐替尼 | Lenvatinib |
| 瑞戈非尼 | Regorafenib |
| ENMD-2076 酒石酸盐 | ENMD-2076 L-(+)-Tartaric acid |
| 普拉替尼 | Telatinib |
| 帕唑帕尼 | Pazopanib |
| 苹果酸卡博替尼 | Cabozantinib malate |
| 瑞格非尼水合物 | Regorafenib Monohydrate |
| 尼达尼布乙磺酸盐 | Nintedanib Ethanesulfonate Salt |
| 乐伐替尼甲磺酸盐 | Lenvatinib Mesylate |
| 西地尼布马来酸盐 | Cediranib Maleate |
| 呋喹替尼 | Fruquintinib |
| 舒你替尼 | Sunitinib |
| 奥莫替尼 | Olmutinib |
| 西特拉瓦替尼 | Sitravatinib |
| 凡德他尼 | Vandetanib |
| 花旗松素 | Taxifolin (Dihydroquercetin) |
| 维生素 E | Vitamin E |
| 吉非替尼 | Gefitinib |
| 阿法替尼 | Afatinib |
| 阿法替尼 | Apatinib |
| 厄洛替尼 | Erlotinib |
| 索拉非尼 | Soragenib |
| 瓦利替尼 | Varlitinib |

The present disclosure will be now further explained with respect to the examples:

Example 1 Sotagliflozin Combined with Gefitinib

1. Determination of the Safe Concentration of Sotagliflozin

The killing effect of Gefitinib on lung cancer A549 cells cultured in sugar-free medium and sugar-containing medium 48 hours after treating A549 cells with 20 μM Gefitinib, trypan blue staining was used to distinguish live cells from dead cells which were stained blue by trypan blue. The result is shown in FIG. 1. Based on the previous findings illustrated in FIG. 1, Sotagliflozin was purchased from Selleck Chemicals for growth inhibition test of cancer cell in vitro. Initially, test using normal human umbilical cord epithelial cells showed that Sotagliflozin produced great cytotoxicity at a concentration higher than 80 μM, and mainly exhibited cell growth inhibition effect at a concentration lower than 80 μM. Therefore, the concentration of Sotagliflozin used in the subsequent compositions of this experiment were lower than 80 μM to avoid affecting normal cells.

2. The Inhibitory Effect of Combination Drugs on Tumor Cells

According to the tissue distribution characteristics of EGFR and SGLT1/2, the targets of Gefitinib and Sotagliflozin, the followings cells were selected for experimental verification: lung cancer cell line A549; colorectal cancer cell line LoVo, HT29, SW620, HCT116; cervical cancer HeLa; ovarian cancer SKOV3; gastric cancer NGC27; cholangiocarcinoma RBE; esophageal cancer KYSE30. After growing to 80% density, the cells were trypsinized, passaged and plated in a 96-well plate with 5000 cells per well. After 24 hours, the medium was replaced with a medium containing the corresponding concentration of drug. After 48 hours, the absorbance at each concentration was detected by the MTT method.

The experiment included the following groups:

Control group: cells were cultured in normal culture medium without drug added.

Gefitinib test group: cells were treated by adding Gefitinib alone at 4 different concentrations, 5 μM, 10 μM, 20 μM, 30 μM, respectively, to the culture medium.

Gefitinib+Sotagliflozin combination test group: cells were treated by adding both Sotagliflozin (20 μM) and Gefitinib at 4 different concentrations, 5 μM, 10 μM, 20 μM and 30 μM, respectively, to the culture medium.

After incubation, the cell growth inhibition rate is calculated by dividing the absorbance value at each concentration by the absorbance value of the control group. The results are shown in FIG. 2-a to FIG. 2-e. In the figure, the concentration of Gefitinib is taken as the abscissa and the cell growth inhibition rate is taken as the ordinate. The results show that the inhibitory effect of Gefitinib alone on tumor cells is limited, and the combination of the two drugs is beneficial to improve the tumor inhibitory effect.

3. Determination of $IC_{50}$ Value of Combination Drugs

Lung cancer cell line A549 was used as an example to verify the $IC_{50}$ value of the Gefitinib+Sotagliflozin combination. The experiment included the following groups:

Gefitinib test group (FIG. 2-a-1): cells were treated by adding Gefitinib alone at 6 different concentrations, 0 μM, 10 μM, 20 μM, 30 μM, 40 μM and 50 μM respectively, to the culture medium, and cell survival rate was measured after 1 h incubation. The results showed that the $IC_{50}$ value of Gefitinib on A549 cells was 24.42 μM.

Sotagliflozin test group (FIG. 2-a-2): cells were treated by adding Sotagliflozin alone at 6 different concentrations, 0 μM, 10 μM, 30 μM, 40 μM, 50 μM and 60 μM respectively, to the culture medium, and cell survival rate was measured after 1 h incubation. The results showed that the $IC_{50}$ value of Sotagliflozin on A549 cells was 73.04 μM.

Gefitinib+Sotagliflozin combination test group 1 (FIG. 2-a-3): cells were treated by adding both Sotagliflozin (10 μM) and Gefitinib at 6 different concentrations, 0 μM, 10 μM, 20 μM, 30 μM, 50 μM and 60 μM respectively, to the culture medium, and cell survival rate was measured after 1 h incubation. The results showed that the $IC_{50}$ value of the test group on A549 cells was 17.03 μM.

Gefitinib+Sotagliflozin combination test group 12 (FIG. 2-a-4): cells were treated by adding both Sotagliflozin (20 μM) and Gefitinib at 5 different concentrations, 0 μM, 10 μM, 20M, 30 μM and 40 μM, respectively, to the culture medium, and cell survival rate was measured after 2 h incubation. The results showed that the $IC_{50}$ value of the test group on A549 cells was 12.71 μM.

Gefitinib+Sotagliflozin combination test group 3 (FIG. 2-a-5): cells were treated by adding both Sotagliflozin (30 μM) and Gefitinib at 6 different concentrations, 0 μM, 10 μM, 20 μM, 30 μM, 40 μM and 50 μM respectively, to the culture medium, and cell survival rate was measured after 1 h incubation. The results showed that the $IC_{50}$ value of the test group on A549 cells was 9.318 μM.

The results showed that with the combination of Sotagliflozin and Gefitinib, the inhibitory rate of Gefitinib on A549 cells was significantly enhanced, and the $IC_{50}$ was reduced to less than half of that of the single agent. Therefore, the effect of the combination in the safe concentration range of Sotagliflozin is better than the effect of each single agent. The verification results of other cell lines are shown in the figures (2f-2j). It is worth mentioning that the ability of Sotagliflozin in the combination to enhance the efficacy of EGFR-targeting TKI drugs is not limited to a single drug of Gefitinib. In FIG. 2k and FIG. 2l, the present disclosure takes A549 cells as an example to further verify the other two inhibitors of EGFR, Afatinib and Erlotinib, and the results show that the addition of Sotagliflozin at a safe dose can effectively reduce $IC_{50}$ values of Afatinib and Erlotinib.

Example 2 Sotagliflozin Combined with Gefitinib Reverses the Resistance of Tumor Cells to Gefitinib 1. Screening of Gefitinib-Resistant Cell Lines.

After knowing that the combination of Gefitinib and Sotagliflozin significantly enhanced the effectiveness of Gefitinib from Example 1, the present disclosure continues to explore whether the combination of the two drugs can reverse the resistance of tumor cells to Gefitinib. Gefitinib-resistant cells can be obtained by long-term culturing of A549 cells with a medium containing Gefitinib at increasing concentration. After 5 months of screening, the present disclosure obtained A549 Gefitinib-resistant cell line that can survive in 60 μM Gefitinib for a long time.

2. Sotagliflozin Combined with Gefitinib Reverses the Resistance of Tumor Cells to Gefitinib The Gefitinib-resistant cell line obtained by the present disclosure can still be effectively killed by adding 30 μM Gefitinib and Sotagliflozin combination. It showed that the combination of Sotagliflozin and Gefitinib reversed the resistance of tumor cells to Gefitinib. The results are shown in FIG. 3.

Example 3 Sotagliflozin Combined with Apatinib

1. The Inhibitory Effect of Combination Drugs on Tumor Cells

After obtaining the effectiveness of Gefitinib in Example 1, the present disclosure further validated another VEGFR-targeting TKI drug, Apatinib. According to the tissue distribution characteristics of VEGFR and SGLT1/2, the targets of Apatinib and Sotagliflozin, the followings cells were selected for experimental verification: liver cancer cell line HepG2; colorectal cancer cell line LoVo, HT29, SW620, SW480; cervical cancer HeLa; ovarian cancer SKOV3; gastric cancer NGC27; cholangiocarcinoma RBE; esophageal cancer KYSE3. After growing to 80% density, the cells were trypsinized, passaged and plated in a 96-well plate with 5000 cells per well. After 24 hours, the medium was replaced with a medium containing the corresponding concentration of Apatinib, Sotagliflozin, or the combination of Apatinib and Sotagliflozin. After 48 hours, the absorbance at each concentration was detected by the MTT method.

The experiment included the following groups:

Control group: cells were cultured in normal culture medium without drug added.

Apatinib test group: cells were treated by adding Apatinib alone at 4 different concentrations, 5 μM, 10 μM, 20 μM, 30 μM, respectively, to the culture medium.

Apatinib+Sotagliflozin combination test group: cells were treated by adding both Sotagliflozin (20 μM) and Apatinib at 4 different concentrations, 5 μM, 10 μM, 20 μM and 30 μM, respectively, to the culture medium.

Figures 1, 2, 4:
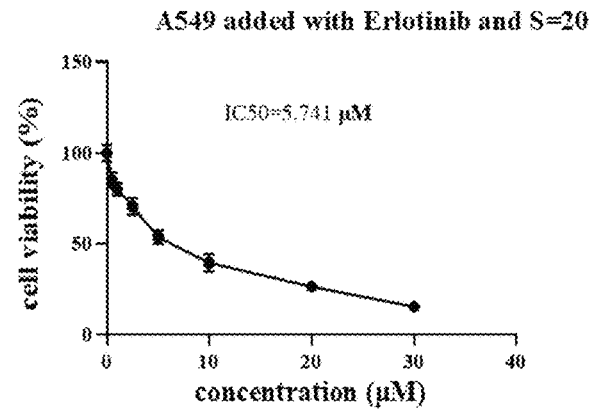
FIG. 4-*a*-1 shows the inhibition effect of Apatinib alone and the combination of Sotagliflozin and Apatinib on the growth of hepatoma cell line HepG2.

The cell growth inhibition rate is calculated by dividing the absorbance value at each concentration by the absorbance value of the control group. The results are shown in FIG. 4-a-1 to FIG. 4-a-5. In the figure, the concentration of Apatinib is taken as the abscissa and the cell growth inhibition rate is taken as the ordinate. The results show that the inhibitory effect of Apatinib alone on tumor cells is limited, and the combination of the two drugs is beneficial to improve the tumor inhibitory effect.

2. Determination of $IC_{50}$ Value of Combination Drugs 2.1. Liver cancer cell line HepG2 was used as an example to verify the $IC_{50}$ value of the Apatinib+Sotagliflozin combination. The experiment included the following groups:

Apatinib test group (FIG. 4-b-1): cells were treated by adding Apatinib alone at 6 different concentrations, 0 μM, 5 μM, 10 μM, 20 μM, 30 μM and 40 μM, respectively, to the culture medium, and cell survival rate was measured after 2 h incubation. The results showed that the $IC_{50}$ value of Apatinib on HepG2 cells was 46.02 μM.

Sotagliflozin test group (FIG. 4-b-2): cells were treated by adding Sotagliflozin alone at 7 different concentrations, 0 μM, 20 μM, 30 μM, 40 μM, 60 μM, 80 μM and 100 μM respectively, to the culture medium, and cell survival rate was measured after 2 h incubation. The results showed that the $IC_{50}$ value of Sotagliflozin on HepG2 cells was 115.7 μM.

Apatinib+Sotagliflozin combination test group 1 (FIG. 4-b-3): cells were treated by adding both Sotagliflozin (10 μM) and Apatinib at 6 different concentrations, 0 μM, 5 μM, 10 μM, 20 μM, 30 μM and 40 μM respectively, to the culture medium, and cell survival rate was measured after 2 h incubation. The results showed that the $IC_{50}$ value of the test group to on HepG2 cells was 33.3 μM.

Apatinib+Sotagliflozin combination test group 2 (FIG. 4-b-4): cells were treated by adding both Sotagliflozin (20 μM) and Apatinib at 6 different concentrations, 0 μM, 5 μM, 10 μM, 20 μM, 30 μM and 40 μM respectively, to the culture medium, and cell survival rate was measured after 2 h incubation. The results showed that the $IC_{50}$ value of the test group to on HepG2 cells was 29.69 μM.

Apatinib+Sotagliflozin combination test group 3 (FIG. 4-b-5): cells were treated by adding both Sotagliflozin (30 μM) and Apatinib at 6 different concentrations, 0 μM, 5 μM, 10 μM, 20 μM, 30 μM and 40 μM respectively, to the culture medium, and cell survival rate was measured after 2 h incubation. The results showed that the $IC_{50}$ value of the test group to on HepG2 cells was 13.13 μM.

Apatinib+Sotagliflozin combination test group 4 (FIG. 4-b-6): cells were treated by adding both Sotagliflozin (40 μM) and Apatinib at 6 different concentrations, 0 μM, 5 μM, 10 μM, 20 μM, 30 μM and 40 μM respectively, to the culture medium, and cell survival rate was measured after 2 h incubation. The results showed that the $IC_{50}$ value of the test group to on HepG2 cells was 10.89 μM.

Figures 1, 2, 5:
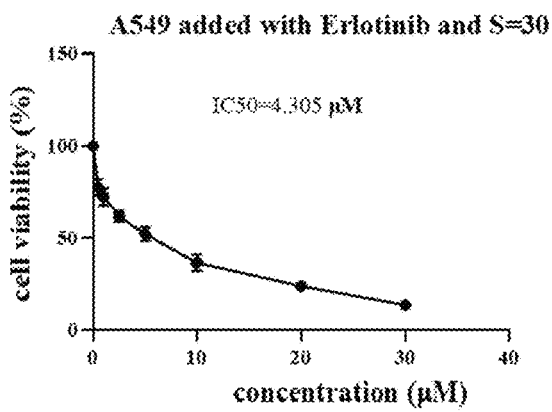
FIG. 5 shows the inhibitory effect of Lenvatinib alone and the composition of Sotagliflozin combined with Lenvatinib on the growth of liver cancer HepG2 cells, colorectal cancer LoVo, HT29, DLD1, SW480, and HCT116 cells.

These results showed that with the combination of Sotagliflozin and Apatinib, the inhibitory rate of Apatinibon on HepG2 cells was significantly enhanced, and the $IC_{50}$ was reduced to less than one-fourth of that of the single agent. Therefore, the effect of the combination in the safe concentration range of Sotagliflozin is better than the effect of each single agent. The verification results of other cell lines are shown in the figures (4c-4g). It is worth mentioning that the ability of Sotagliflozin in the combination to enhance the efficacy of VEGFR-targeting TKI drugs is not limited to a single drug of Apatinib. In FIG. 5, the present disclosure further verified another VEGFR inhibitor Lenvatinib in a variety of cell lines, and the results showed that the addition of Sotagliflozin at a safe dose enhanced the inhibitory effect of Lenvatinib on these cell lines.

Example 4

Other TKI drugs were further verified, proving that the TKI drugs which can be combined with Sotagliflozin are not limited to specific one or several drugs.

Figures 1, 2, 6:
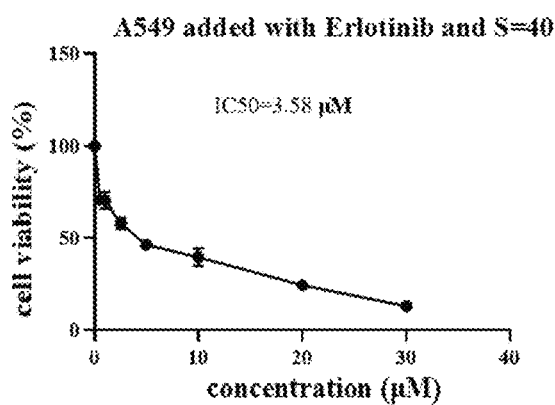
Figure 3:
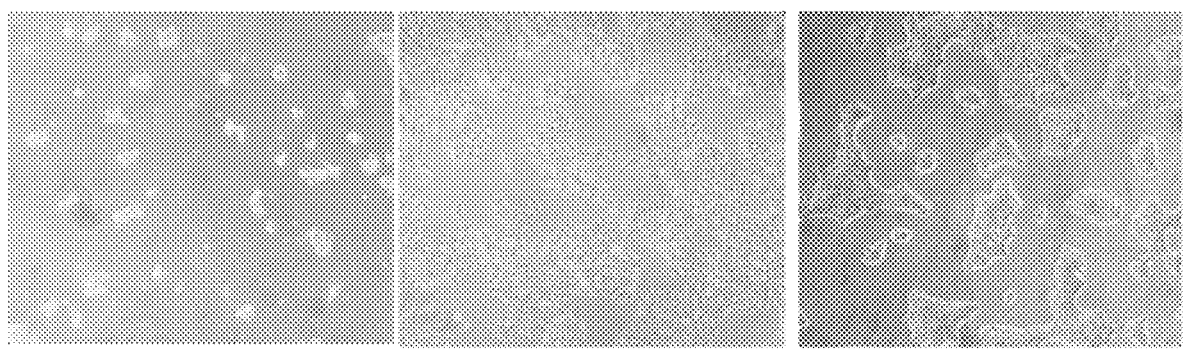
Figure 5:
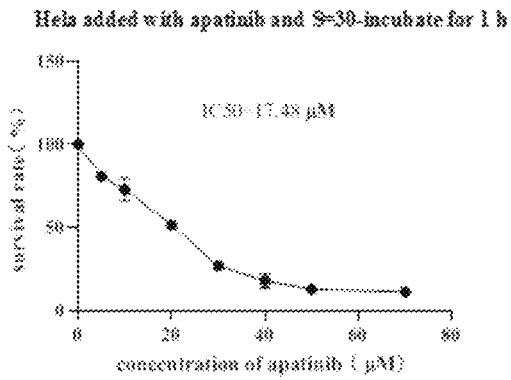
Figure 5:
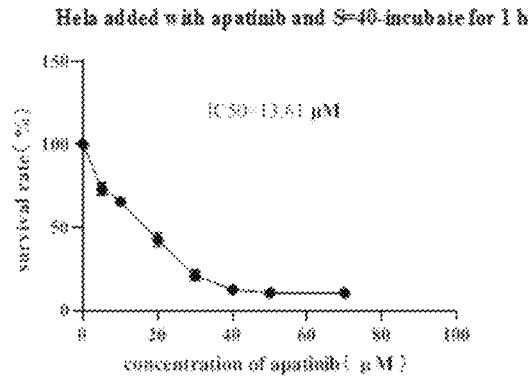
Figure 5:
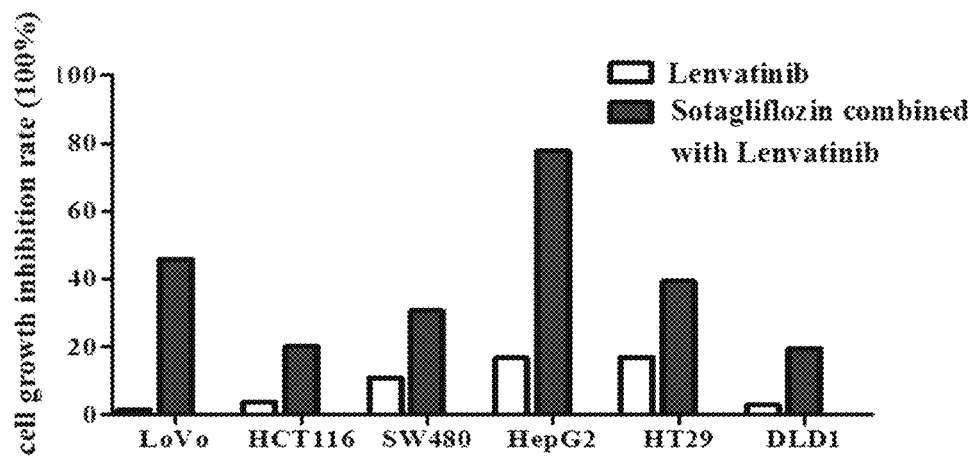

The selected drugs included: Axitinib (FIG. 6-1), Nintedanib (FIG. 6-2), Cediranib (FIG. 6-3), Pazopanib HCl (FIG. 6-4), Sunitinib Malate (FIG. 6-5), Brivanib (FIG. 6-6), Cabozantinib (FIG. 6-7), Brivanib alaninate (FIG. 6-8), Lenvatinib (FIG. 6-9), Regorafenib (FIG. 6-10), ENMD-2076 (FIG. 6-11), Tivozanib (FIG. 6-12), Ponatinib (FIG. 6-13), ENMD-2076 L-(+)-tartaric acid (FIG. 6-14), Telatinib (FIG. 6-15), Taxifolin (FIG. 6-16), Pazopanib (FIG. 6-17), Cabozantinib malate (FIG. 6-18), Vitamin E (FIG. 6-19), Regorafenib monohydrate (FIG. 6-20), Nintedanib ethanesulfonate salt (FIG. 6-21), Lenvatinib mesylate (FIG. 6-22), Cediranib maleate (FIG. 6-23), LY2874455 (FIG. 6-24), Sunitinib (FIG. 6-25), Sitravatinib (FIG. 6-26), Anlotinib (FIG. 6-27), Sorafenib (FIG. 6-28), Vandetanib (FIG. 6-29), Fruquintinib (FIG. 6-30), Olmutinib (FIG. 6-31), Osimertinib (FIG. 6-32), Genistein (FIG. 6-33), Avitinib (FIG. 6-34), DacOlmutinib (FIG. 6-35), Osimertinib mesylate (FIG. 6-36), Daphnetin (FIG. 6-37), Varlitinib (FIG. 6-38), AZD3759 (FIG. 6-39), Lazertinib (FIG. 6-40), Nazartinib (FIG. 6-41), Lidocaine hydrochloride (FIG. 6-42), and Icotinib (FIG. 6-43).

The present disclosure preferentially selected liver cancer cell line HepG2 for experimental verification. After growing to 80/density, the cells were trypsinized, passaged and plated in a 96-well plate with 5000 cells per well. After 24 hours, the medium was replaced with a medium containing the corresponding concentration of Apatinib, Sotagliflozin, or the combination of Apatinib and Sotagliflozin. After 48 hours, the absorbance at each concentration was detected by the MTT method.

The experimental method was the same as before, and the incubation time was 1 h. The experiment included a blank control group, namely normal cultured HepG2 cells, in which the concentration of Sotagliflozin or TKI drugs was 0, and the survival rate of the blank control group cells was set to 100%. In other groups, the concentration of Sotagliflozin used was 30 μmol/L, and the concentrations of TKI drugs are shown in Table 2. The results are shown in the attached Figure:

TABLE 2

Experimental design of the administration group

| Group | Group 1 | Group 2 | Group 3 | Group 4 |
|---|---|---|---|---|
| Axitinib | Sotagliflozin 30 μmol/L + Axitinib 0 | Sotagliflozin 30 μmol/L + Axitinib 0.1 μmol/L | — | — |
| Brivanib Alaninate | Sotagliflozin 30 μmol/L + Brivanib Alaninate 0 | Sotagliflozin 30 μmol/L + Brivanib Alaninate 0.1 μmol/L | Sotagliflozin 30 μmol/L + Brivanib Alaninate 2.5 μmol/L | — |
| Pazopanib | Sotagliflozin 30 μmol/L + Pazopanib 0 | Sotagliflozin 30 μmol/L + Pazopanib 0.1 μmol/L | — | — |
| Cediranib Maleate | Sotagliflozin 30 μmol/L + Cediranib Maleate 0 | Sotagliflozin 30 μmol/L + Cediranib Maleate 0.5 μmol/L | — | — |
| Olmutinib | Sotagliflozin 30 μmol/L + Olmutinib 0 | Sotagliflozin 30 μmol/L + Olmutinib 0.1 μmol/L | Sotagliflozin 30 μmol/L + Olmutinib 2.5 μmol/L | — |
| Nintedanib | Sotagliflozin 30 μmol/L + Nintedanib 0 | Sotagliflozin 30 μmol/L + Nintedanib 0.1 μmol/L | Sotagliflozin 30 μmol/L + Nintedanib 10 μmol/L | — |
| Lenvatinib | Sotagliflozin 30 μmol/L + Lenvatinib 0 | Sotagliflozin 30 μmol/L + Lenvatinib 0.1 μmol/L | Sotagliflozin 30 μmol/L + Lenvatinib 10 μmol/L | — |
| Cabozantinib malate | Sotagliflozin 30 μmol/L + Cabozantinib malate 0 | Sotagliflozin 30 μmol/L + Cabozantinib malate 0.1 μmol/L | Sotagliflozin 30 μmol/L + Cabozantinib malate 10 μmol/L | — |
| Soragenib | Sotagliflozin 30 μmol/L + Soragenib 0 | Sotagliflozin 30 μmol/L + Soragenib 0.1 μmol/L | Sotagliflozin 30 μmol/L + Soragenib 10 μmol/L | — |
| Cediranib | Sotagliflozin 30 μmol/L + Cediranib 0 | Sotagliflozin 30 μmol/L + Cediranib 0.5 μmol/L | Sotagliflozin 30 μmol/L + Cediranib 10 μmol/L | — |
| Regorafenib | Sotagliflozin 30 μmol/L + Regorafenib 0 | Sotagliflozin 30 μmol/L + Regorafenib 0.1 μmol/L | Sotagliflozin 30 μmol/L + Regorafenib 10 μmol/L | — |
| Telatinib | Sotagliflozin 30 μmol/L + Telatinib 0 | Sotagliflozin 30 μmol/L + Telatinib 0.1 μmol/L | Sotagliflozin 30 μmol/L + Telatinib 10 μmol/L | — |
| Lidocaine hydrochloride | Sotagliflozin 30 μmol/L + Lidocaine hydrochloride 0 | Sotagliflozin 30 μmol/L + Lidocaine hydrochloride 2.5 μmol/L | — | — |
| LY2874455 | Sotagliflozin 30 μmol/L + LY2874455 0 | Sotagliflozin 30 μmol/L + LY2874455 0.1 μmol/L | — | — |
| Sitravatinib | Sotagliflozin 30 μmol/L + Sitravatinib 0 | Sotagliflozin 30 μmol/L + Sitravatinib 0.1 μmol/L | — | — |
| ENMD-2076 | Sotagliflozin 30 μmol/L + ENMD-2076 0 | Sotagliflozin 30 μmol/L + ENMD-2076 0.1 μmol/L | — | — |
| Taxifolin | Sotagliflozin 30 μmol/L + Taxifolin 0 | Sotagliflozin 30 μmol/L + Taxifolin 0.1 μmol/L | — | — |
| Vitamin E | Sotagliflozin 30 μmol/L + Vitamin E 0 | Sotagliflozin 30 μmol/L + Vitamin E 0.1 μmol/L | — | — |
| Osimertinib | Sotagliflozin 30 μmol/L + Osimertinib 0 | Sotagliflozin 30 μmol/L + Osimertinib 0.1 μmol/L | Sotagliflozin 30 μmol/L + Osimertinib 2.5 μmol/L | — |
| Anlotinib dihydrochloride | Sotagliflozin 30 μmol/L + Anlotinib dihydrochloride 0 | Sotagliflozin 30 μmol/L + Anlotinib dihydrochloride 0.1 μmol/L | Sotagliflozin 30 μmol/L + Anlotinib dihydrochloride 2.5 μmol/L | Sotagliflozin 30 μmol/L + Anlotinib dihydrochloride 25 μmol/L |
| Pazopanib HCl | Sotagliflozin 30 μmol/L + Pazopanib HCl 0 | Sotagliflozin 30 μmol/L + Pazopanib HCl 0.1 μmol/L | Sotagliflozin 30 μmol/L + Pazopanib HCl 10 μmol/L | — |

TABLE 2-continued

Experimental design of the administration group

| Group | Group 1 | Group 2 | Group 3 | Group 4 |
|---|---|---|---|---|
| Tivozanib | Sotagliflozin 30 μmol/L + Tivozanib 0 | Sotagliflozin 30 μmol/L + Tivozanib 0.1 μmol/L | Sotagliflozin 30 μmol/L + Tivozanib 25 μmol/L | — |
| Regorafenib Monohydrate | Sotagliflozin 30 μmol/L + Regorafenib monohydrate 0 | Sotagliflozin 30 μmol/L + Regorafenib Monohydrate 0.1 μmol/L | Sotagliflozin 30 μmol/L + Regorafenib Monohydrate 10 μmol/L | — |
| Avitinib | Sotagliflozin 30 μmol/L + Avitinib 0 | Sotagliflozin 30 μmol/L + Avitinib 0.1 μmol/L | — | — |
| Sunitinib Malate | Sotagliflozin 30 μmol/L + Sunitinib malate 0 | Sotagliflozin 30 μmol/L + Sunitinib Malate 0.1 μmol/L | Sotagliflozin 30 μmol/L + Sunitinib malate 2.5 μmol/L | — |
| Genistein | Sotagliflozin 30 μmol/L + Genistein 0 | Sotagliflozin 30 μmol/L + Genistein 0.1 μmol/L | — | — |
| DacOlmutinib | Sotagliflozin 30 μmol/L + DacOlmutinib 0 | Sotagliflozin 30 μmol/L + DacOlmutinib 0.1 μmol/L | Sotagliflozin 30 μmol/L + DacOlmutinib 2.5 μmol/L | — |
| Osimertinib mesylate | Sotagliflozin 30 μmol/L + Osimertinib mesylate 0 | Sotagliflozin 30 μmol/L + Osimertinib mesylate 0.1 μmol/L | — | — |
| Sunitinib | Sotagliflozin 30 μmol/L + Sunitinib 0 | Sotagliflozin 30 μmol/L + Sunitinib 0.1 μmol/L | Sotagliflozin 30 μmol/L + Sunitinib 10 μmol/L | — |
| Vandetanib | Sotagliflozin 30 μmol/L + Vandetanib 0 | Sotagliflozin 30 μmol/L + Vandetanib 0.1 μmol/L | Sotagliflozin 30 μmol/L + Vandetanib 25 μmol/L | Sotagliflozin 30 μmol/L + Vandetanib 50 μmol/L |
| Brivanib | Sotagliflozin 30 μmol/L + Brivanib 0 | Sotagliflozin 30 μmol/L + Brivanib 0.1 μmol/L | Sotagliflozin 30 μmol/L + Brivanib 10 μmol/L | Sotagliflozin 30 μmol/L + Brivanib 50 μmol/L |
| Ponatinib | Sotagliflozin 30 μmol/L + Ponatinib 0 | Sotagliflozin 30 μmol/L + Ponatinib 0.1 μmol/L | — | — |
| Varlitinib | Sotagliflozin 30 μmol/L + Varlitinib 0 | Sotagliflozin 30 μmol/L + Varlitinib 0.1 μmol/L | Sotagliflozin 30 μmol/L + Varlitinib 10 μmol/L | — |
| Nintedanib Ethanesulfonate | Sotagliflozin 30 μmol/L + Nintedanib ethanesulfonate 0 | Sotagliflozin 30 μmol/L + Nintedanib Ethanesulfonate 0.1 μmol/L | Sotagliflozin 30 μmol/L + Nintedanib Ethanesulfonate 10 μmol/L | — |
| Nazartinib | Sotagliflozin 30 μmol/L + Nazartinib 0 | Sotagliflozin 30 μmol/L + Nazartinib 0.1 μmol/L | Sotagliflozin 30 μmol/L + Nazartinib 10 μmol/L | — |
| Cabozantinib | Sotagliflozin 30 μmol/L + Cabozantinib 0 | Sotagliflozin 30 μmol/L + Cabozantinib 0.1 μmol/L | Sotagliflozin 30 μmol/L + Cabozantinib 10 μmol/L | — |
| ENMD-2076 L-(+)-TARTARIC ACID | Sotagliflozin 30 μmol/L + ENMD-2076 L-(+)-TARTARIC ACID 0 | Sotagliflozin 30 μmol/L + ENMD-2076 L-(+)-TARTARIC ACID 0.1 μmol/L | Sotagliflozin 30 μmol/L + ENMD-2076 L-(+)-TARTARIC ACID 10 μmol/L | — |
| Icotinib | Sotagliflozin 30 μmol/L + Icotinib 0 | Sotagliflozin 30 μmol/L + Icotinib 2.5 μmol/L | — | — |
| Lenvatinib Mesylate | Sotagliflozin 30 μmol/L + Lenvatinib mesylate 0 | Sotagliflozin 30 μmol/L + Lenvatinib Mesylate 0.1 μmol/L | Sotagliflozin 30 μmol/L + Lenvatinib mesylate 10 μmol/L | Sotagliflozin 30 μmol/L + Lenvatinib mesylate 50 μmol/L |
| AZD3759 | Sotagliflozin 30 μmol/L + AZD3759 0 | Sotagliflozin 30 μmol/L + AZD3759 0.1 μmol/L | Sotagliflozin 30 μmol/L + AZD3759 10 μmol/L | Sotagliflozin 30 μmol/L + AZD3759 50 μmol/L |
| Lazertinib | Sotagliflozin 30 μmol/L + Lazertinib 0 | Sotagliflozin 30 μmol/L + Lazertinib 0.1 μmol/L | Sotagliflozin 30 μmol/L + Lazertinib 0.5 μmol/L | — |

These results showed that each combination administration group showed a significantly better inhibitory effect on tumor cells than the single agent control group.

Example 5

Examples 1 to 4 are tests at the cell level. In order to further verify the in vivo anti-tumor effect of the diabetes treatment drug Sotagliflozin discovered in the present disclosure and the combination thereof with TKI inhibitor drugs, lung cancer A549 cells and the Balbc nude mice from Charles River Laboratories were used in tumor treatment trials. After growing to the logarithmic phase, A549 cells were collected and resuspended in serum-free DMEM medium to $5 \times 10^7$ cells per ml. Each mouse was inoculated with 100 μl of $5 \times 10^6$ cells, and the tumor size was measured 19 days later. Mice were grouped according to the tumor size, and the average tumor size in each group was the same. Mice were administered after grouping. According to the current recommended daily dose 200-400 mg of Sotagliflozin for diabetic patients, corresponding to 22 mg to 44 mg drug per kilogram of body weight for mice, we finally chose a dose of 30 mg Sotagliflozin per kilogram for oral administration in mice. The dosage of Gefitinib was 100 mg per kilogram according to the reported dose for the treatment of A549 xenografts in previous studies. The two drugs were administered by gavage, consistent with the current oral mode in clinical use. The dosing cycle was once every two days. The tumor size was measured every two days. After 40 days of administration, the test was ended, and the tumor was removed and weighed.

TABLE 3

Summary of the efficacy of Sotagliflozin combined
with Gefitinib on A549 tumor cell-bearing mice

| | Average tumor volume | Tumor volume ratio of each group to the control group | Tumor growth inhibition rate | p value |
|---|---|---|---|---|
| Solvent control group | 1034.278808 | | | |
| Sotagliflozin | 430.2976498 | 0.416036417 | 58.39635826 | 0.002 |
| Gefitinib | 504.8082165 | 0.488077502 | 51.19224984 | 0.0012 |
| Sotagliflozin combined with Gefitinib | 211.0447064 | 0.204050112 | 79.59498882 | 0.0001 |

Figures 1, 6:
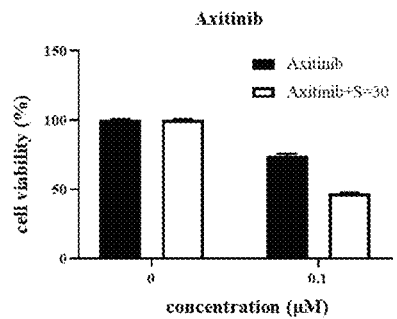
Figures 2, 6:
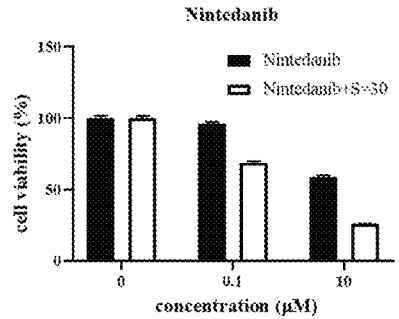
Figures 3, 6:
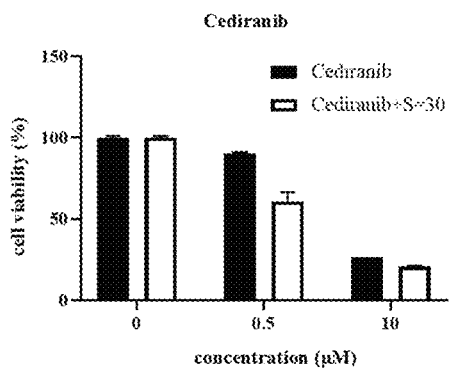
Figures 4, 6:
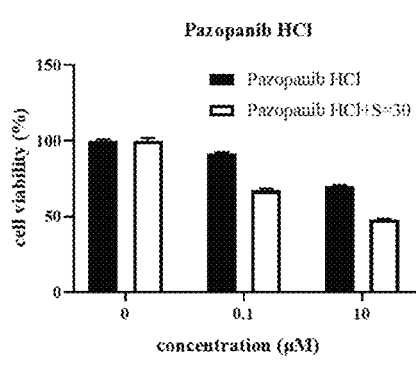
Figures 5, 6:
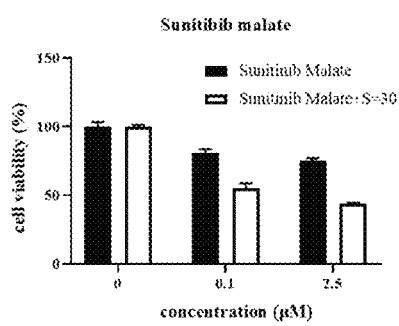
Figure 6:
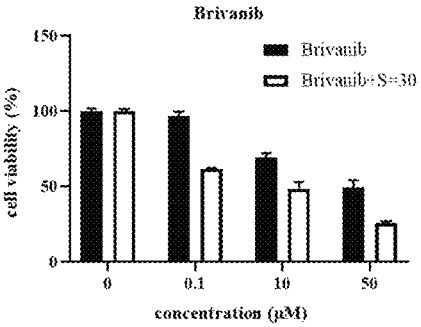
Figures 6, 7:
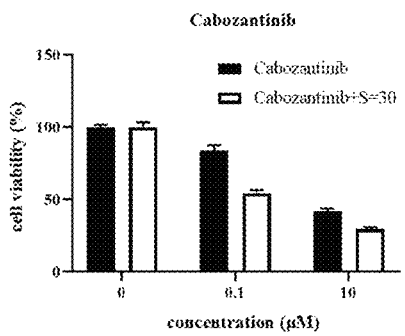
Figures 6, 7, 8:
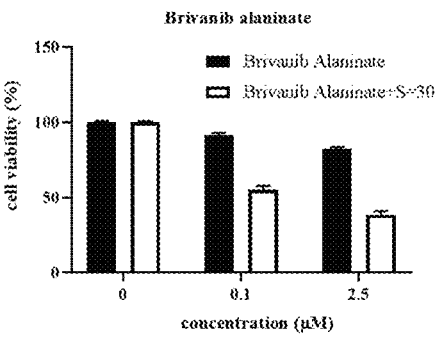
Figures 6, 7, 8, 9:
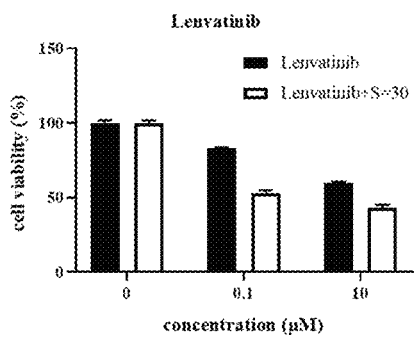
Figures 6, 7, 8, 9, 10:
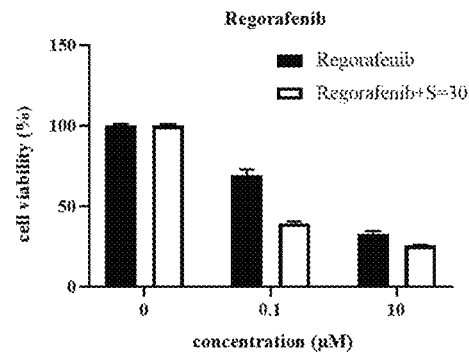
Figures 6, 7, 8, 9, 10, 11:
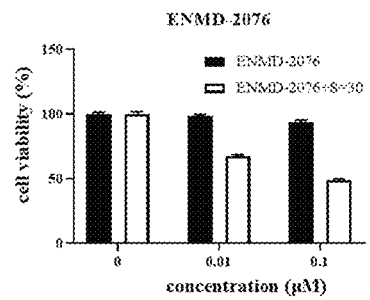
Figures 6, 7, 8, 9, 10, 11, 12:
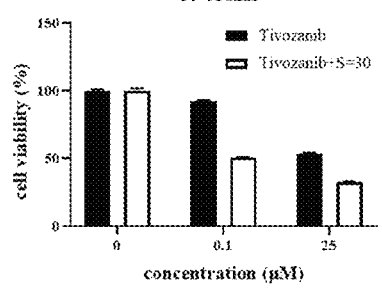
Figures 6, 7, 8, 9, 10, 11, 12, 13:
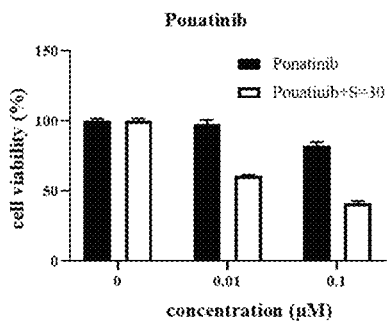
Figures 6, 7, 8, 9, 10, 11, 12, 13, 14:
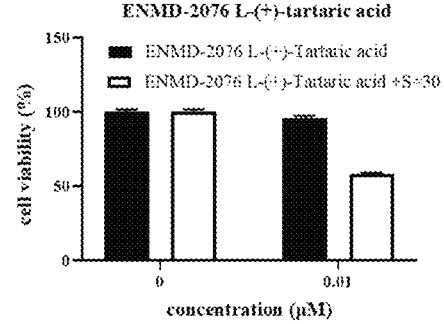
Figures 6, 7, 8, 9, 10, 11, 12, 13, 14, 15:
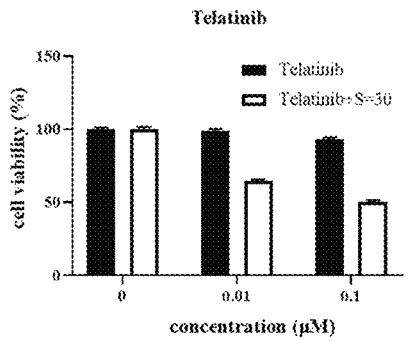
Figures 6, 7, 8, 9, 10, 11, 12, 13, 14, 15, 16:
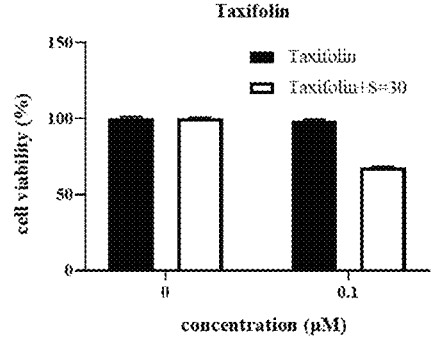
Figures 6, 7, 8, 9, 10, 11, 12, 13, 14, 15, 16, 17:
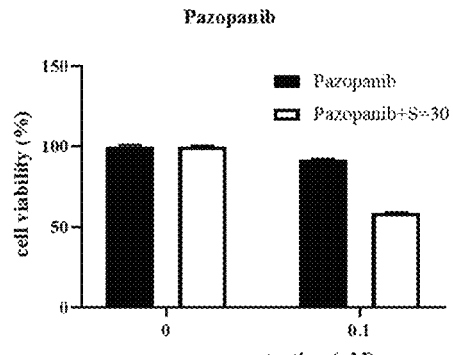
Figures 6, 7, 8, 9, 10, 11, 12, 13, 14, 15, 16, 17, 18:
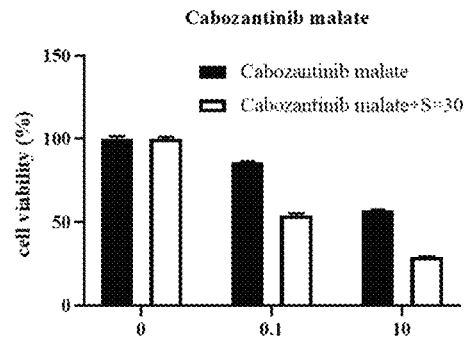
Figures 6, 7, 8, 9, 10, 11, 12, 13, 14, 15, 16, 17, 18, 19:
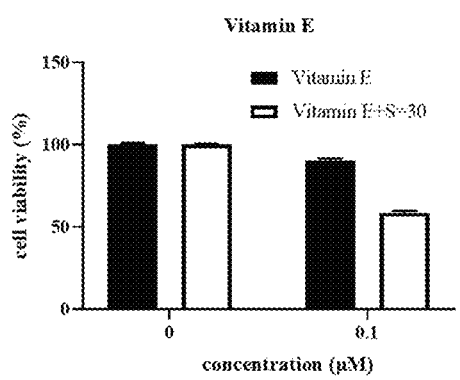
Figures 6, 7, 8, 9, 10, 11, 12, 13, 14, 15, 16, 17, 18, 19, 20:
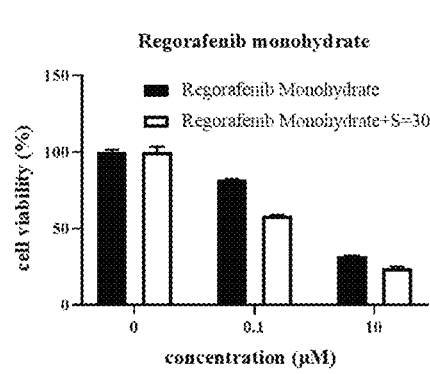
Figures 6, 7, 8, 9, 10, 11, 12, 13, 14, 15, 16, 17, 18, 19, 20, 21:
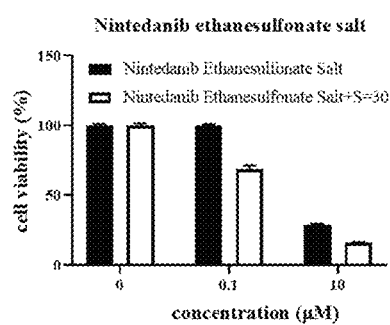
Figures 6, 7, 8, 9, 10, 11, 12, 13, 14, 15, 16, 17, 18, 19, 20, 21, 22:
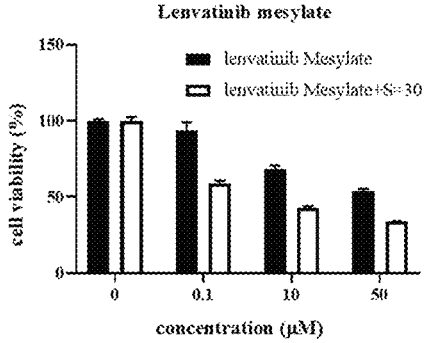
Figures 6, 7, 8, 9, 10, 11, 12, 13, 14, 15, 16, 17, 18, 19, 20, 21, 22, 23:
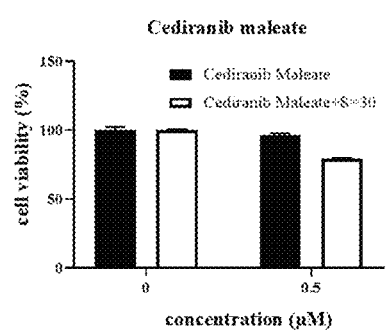
Figures 6, 7, 8, 9, 10, 11, 12, 13, 14, 15, 16, 17, 18, 19, 20, 21, 22, 23, 24:
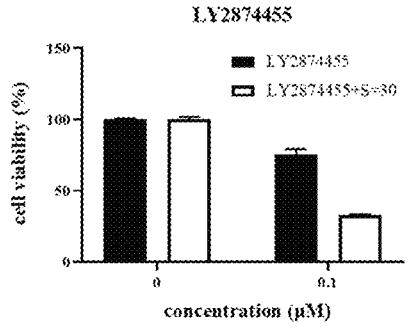
Figures 6, 7, 8, 9, 10, 11, 12, 13, 14, 15, 16, 17, 18, 19, 20, 21, 22, 23, 24, 25:
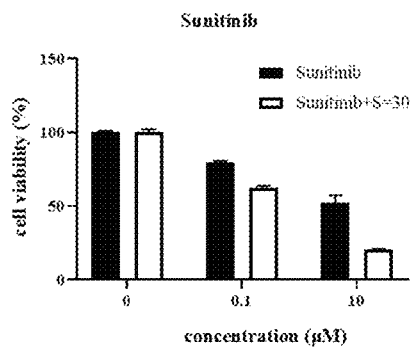
Figures 6, 7, 8, 9, 10, 11, 12, 13, 14, 15, 16, 17, 18, 19, 20, 21, 22, 23, 24, 25, 26:
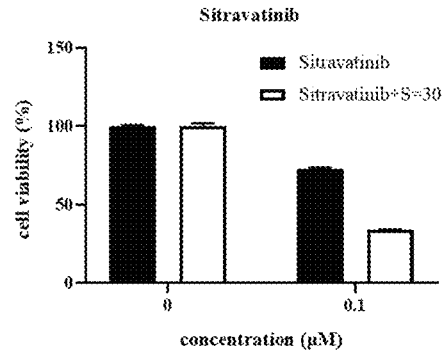
Figures 6, 7, 8, 9, 10, 11, 12, 13, 14, 15, 16, 17, 18, 19, 20, 21, 22, 23, 24, 25, 26, 27:
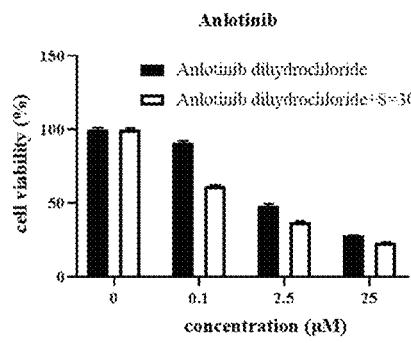
Figures 6, 7, 8, 9, 10, 11, 12, 13, 14, 15, 16, 17, 18, 19, 20, 21, 22, 23, 24, 25, 26, 27, 28:
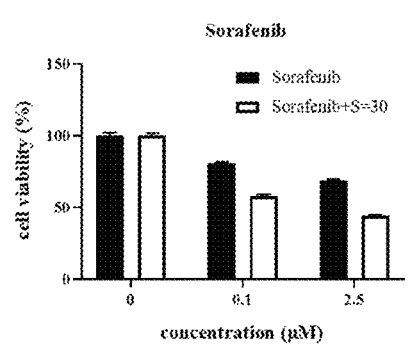
Figures 6, 7, 8, 9, 10, 11, 12, 13, 14, 15, 16, 17, 18, 19, 20, 21, 22, 23, 24, 25, 26, 27, 28, 29:
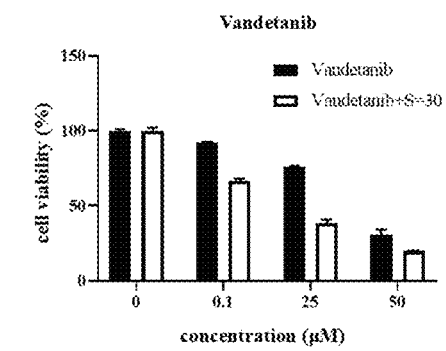
Figures 6, 7, 8, 9, 10, 11, 12, 13, 14, 15, 16, 17, 18, 19, 20, 21, 22, 23, 24, 25, 26, 27, 28, 29, 30:
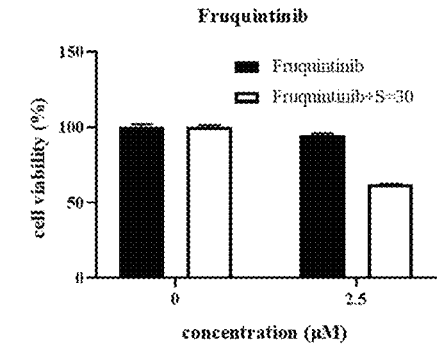
Figures 6, 7, 8, 9, 10, 11, 12, 13, 14, 15, 16, 17, 18, 19, 20, 21, 22, 23, 24, 25, 26, 27, 28, 29, 30, 31:
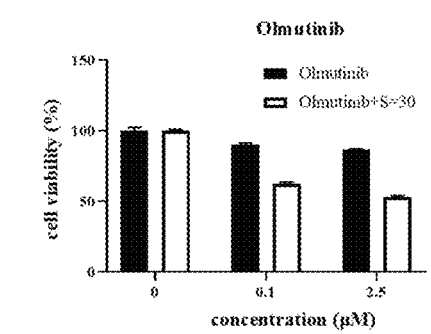
Figures 6, 7, 8, 9, 10, 11, 12, 13, 14, 15, 16, 17, 18, 19, 20, 21, 22, 23, 24, 25, 26, 27, 28, 29, 30, 31, 32:
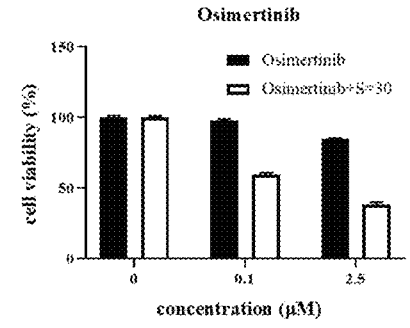
Figures 6, 7, 8, 9, 10, 11, 12, 13, 14, 15, 16, 17, 18, 19, 20, 21, 22, 23, 24, 25, 26, 27, 28, 29, 30, 31, 32, 33:
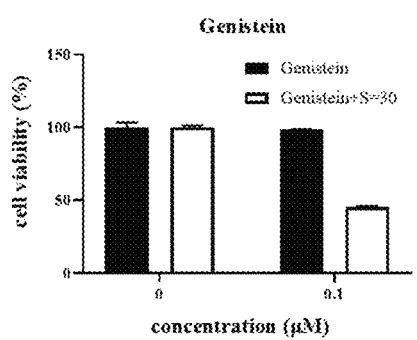
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34:
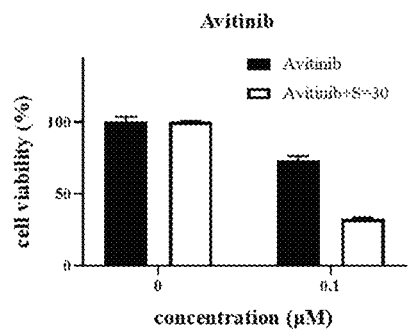
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
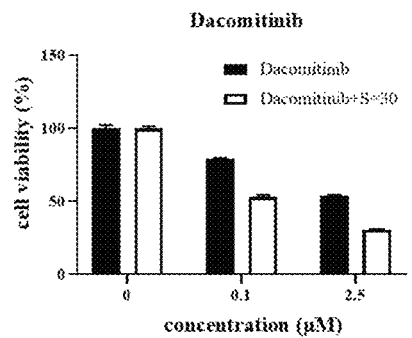
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
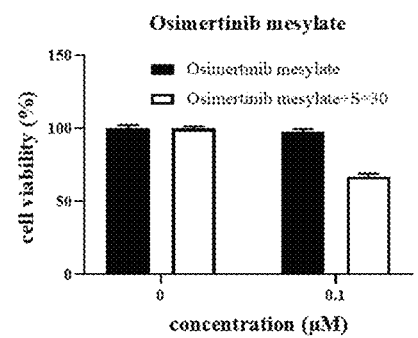
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
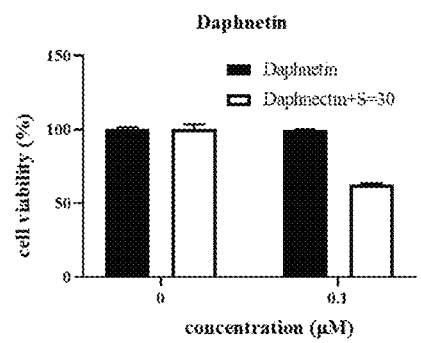
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
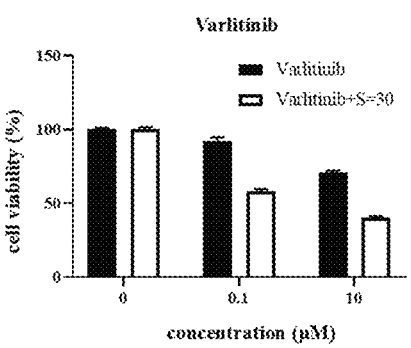
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
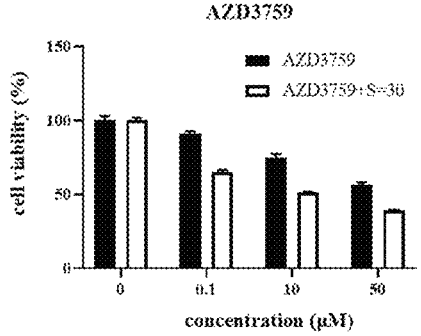
Figures 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
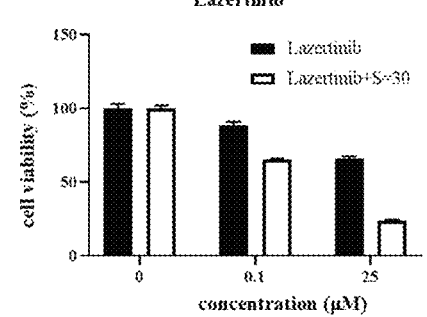

As shown in FIG. 7-a~FIG. 7-b~FIG. 7-c, both Sotagliflozin and Gefitinib can inhibit tumor growth (FIG. 7-a~FIG. 7-b~FIG. 7-c), and the inhibitory effect of the combination of Sotagliflozin and Gefitinib on tumors is better than that of the either drug alone. In order to meet the effectiveness evaluation, the tumor growth inhibition rate should be greater than 60%, and the p value should be less than 0.05. The calculated tumor growth inhibition rate and p value of each group are as shown in the above table. Therefore, the administration of Sotagliflozin or Gefitinib alone is ineffective, and the administration of the combination of Sotagliflozin and Gefitinib is effective.

The above are only the preferred embodiments of the present disclosure. It should be pointed out that for those of ordinary skill in the art, various improvements and modifications can be made without departing from the principle of the present disclosure, and these improvements and modifications should also be considered within the scope of the present disclosure.

The invention claimed is:

1. A composition comprising
    Sotagliflozin or a pharmaceutically acceptable salt, dimer or trimer thereof; and
    a tyrosine kinase activity inhibitor.

2. The composition according to claim 1, wherein the tyrosine kinase activity inhibitor is selected from the group consisting of EGFR inhibitor, c-Kit, c-Met, c-Ret, Raf, PDGFR, BTK, PKA/C, FGFR inhibitor and VEGFR inhibitor.

3. The composition according to claim 2, wherein the tyrosine kinase activity inhibitor is at least one of ENMD-2076, Tivozanib, Genistein, Ponatinib, Daphnetin, DacOlmutinib, Varlitinib, Icotinib, Osimertinib mesylate, Osimertinib, Nazartinib, AZD3759, Anlotinib, Avitinib, Lazertinib, Lidocaine hydrochloride, 4-[(1E)-2-[5-[(1R)-1-(3,5-dichloro-4-pyridyl)ethoxy]-1H-indazol-3-yl]vinyl]-1H-pyrazole-1-ethanol, Axitinib, Nintedanib, Cediranib, Pazopanib HCl, Sunitinib malate, Brivanib, Cabozantinib, Brivanib Alaninate, Lenvatinib, Regorafenib, ENMD-2076 L-(+)-Tartaric acid, Telatinib, Pazopanib, Cabozantinib malate, Regorafenib monohydrate, Nintedanib Ethanesulfonate salt, Lenvatinib mesylate, Cediranib maleate, Fruquintinib, Sunitinib, Olmutinib, Sitravatinib, Vandetanib, Gefitinib, Afatinib, Apatinib, Erlotinib, Sorafenib, Taxifolin or Vitamin E.

4. The composition according to claim 1, wherein the molar ratio of Sotagliflozin or a pharmaceutically acceptable salt, dimer or trimer thereof to the tyrosine kinase activity inhibitor is (10~40): (5~60).

5. A medicament for relieving symptoms of cancer, comprising the composition according to claim 1, wherein the cancer is selected from the group consisting of lung cancer, colorectal cancer, cervical cancer, ovarian cancer, cholangiocarcinoma, gastric cancer, esophageal cancer, and liver cancer.

6. The medicament according to claim 5, wherein the medicament is administered orally, and its dosage form is selected from the group consisting of granules, pills, powders, tablets, capsules, oral solutions and syrups.

7. A method of relieving symptoms of cancer, comprising administering a subject in need thereof the composition according to claim 1, wherein the cancer is selected from the group consisting of lung cancer, colorectal cancer, cervical cancer, ovarian cancer, cholangiocarcinoma, gastric cancer, esophageal cancer, and liver cancer.

8. The method according to claim 7, wherein the treatment comprises inhibiting tumor cell proliferation and/or inhibiting tumor volume.

* * * * *